United States Patent
Silvo et al.

(10) Patent No.: US 10,155,645 B2
(45) Date of Patent: Dec. 18, 2018

(54) MONITORING CONDITION OF ELONGATED FERROUS OBJECT HAVING A LONGITUDINAL AXIS

(71) Applicant: KONECRANES GLOBAL CORPORATION, Hyvinkää (FI)

(72) Inventors: Joni Silvo, Helsinki (FI); Matti Pekkarinen, Espoo (FI); Jack Hoover, Hyvinkää (FI); Mats Åkesson, Hyvinkää (FI); Matti Kumpulainen, Pyhäntä (FI); Jyrki Savela, Oulu (FI)

(73) Assignee: KONECRANES GLOBAL CORPORATION, Hyvinkää (FI)

( * ) Notice: Subject to any disclaimer, the term of this patent is extended or adjusted under 35 U.S.C. 154(b) by 429 days.

(21) Appl. No.: 15/035,437

(22) PCT Filed: Nov. 12, 2014

(86) PCT No.: PCT/FI2014/050855
§ 371 (c)(1),
(2) Date: May 9, 2016

(87) PCT Pub. No.: WO2015/071541
PCT Pub. Date: May 21, 2015

(65) Prior Publication Data
US 2016/0325970 A1    Nov. 10, 2016

(30) Foreign Application Priority Data
Nov. 12, 2013   (FI) ..................................... 20136109

(51) Int. Cl.
*B66C 15/06*       (2006.01)
*G01N 27/83*       (2006.01)
*B66B 7/12*        (2006.01)

(52) U.S. Cl.
CPC ............ *B66C 15/065* (2013.01); *B66B 7/123* (2013.01); *G01N 27/83* (2013.01)

(58) Field of Classification Search
CPC ......... B61B 12/06; B65G 43/02; B66B 7/123; B66C 15/06; B66C 15/065; B66D 1/54;
(Continued)

(56) References Cited

U.S. PATENT DOCUMENTS 4,096,437 A    6/1978  Kitzinger et al.
4,495,465 A *  1/1985  Tomaiuolo ............. G01R 33/12
                                                    324/232
(Continued)

FOREIGN PATENT DOCUMENTS

CA    1 182 172 A    2/1985
CA    1 999 701 A    1/1986
(Continued)

OTHER PUBLICATIONS

Chinese Office Action and Search Report, dated Jul. 3, 2018 for Chinese Application No. 201480071534.1, with English translations.

*Primary Examiner* — Jermele M Hollington
*Assistant Examiner* — Steven Yeninas
(74) *Attorney, Agent, or Firm* — Birch, Stewart, Kolasch & Birch, LLP

(57) ABSTRACT

There is provided an apparatus, a monitoring arrangement, a method, a crane and a tool for monitoring a condition of an elongated ferrous object having a longitudinal axis. Two magnetizing circuits including magnetic poles are arranged along the longitudinal axis of the object. A magnetic flux guide connects the poles. The magnetizing circuits are arranged around the object at opposite sides along the longitudinal axis, wherein the magnetizing circuits are hinged together to be movable between a closed position,
(Continued)

where the object is enclosed between the poles of the magnetizing circuits and an open position, where monitored object is removable from the apparatus. The apparatus includes an enforcing element operatively connected to the magnetizing circuits such that, in the closed position, the magnetizing circuits are pressed towards each other; and the operative connection between the enforcing element and the magnetizing circuits is caused to disconnect on the basis of detecting a faulty portion of the longitudinal ferrous object by a force received from a faulty portion of the longitudinal ferrous object.

25 Claims, 5 Drawing Sheets

(58) Field of Classification Search
CPC .......... G01B 7/12; G01B 7/125; G01B 11/08; G01B 11/10; G01N 27/72; G01N 27/82; G01N 27/83; G01N 29/04; G01N 2291/2626; G01R 33/0011
USPC .......... 73/643; 324/225–230, 235, 237, 238, 324/240–243, 260–262
See application file for complete search history.

(56) References Cited

U.S. PATENT DOCUMENTS

| | | | | |
|---|---|---|---|---|
| 4,546,316 A * | 10/1985 | Lang | .................... | G01N 27/902 324/240 |
| 4,601,221 A | 7/1986 | Kalkbrenner et al. | | |
| 4,686,906 A * | 8/1987 | Meindl | ................. | B61B 12/122 104/204 |
| 4,827,215 A * | 5/1989 | van der Walt | ......... | G01N 27/82 324/227 |
| 4,889,021 A | 12/1989 | Morrison | | |
| 5,052,251 A | 10/1991 | Mills | | |
| 5,321,356 A * | 6/1994 | Weischedel | ............ | G01N 27/82 324/240 |
| 5,414,353 A | 5/1995 | Weischedel | | |
| 5,828,213 A * | 10/1998 | Hickman | ................ | G01N 27/82 324/235 |
| 6,265,870 B1 * | 7/2001 | Weischedel | .......... | G01N 27/902 324/220 |
| 2010/0244821 A1 | 9/2010 | Nishiyori et al. | | |
| 2014/0027401 A1 | 1/2014 | Ilaka et al. | | |

FOREIGN PATENT DOCUMENTS

| | | |
|---|---|---|
| CN | 101013106 A | 8/2007 |
| CN | 101513729 A | 8/2009 |
| CN | 101855159 A | 10/2010 |
| EP | 0 093 566 A2 | 11/1983 |
| EP | 0 816 797 A2 | 1/1998 |
| EP | 2 581 289 A1 | 4/2013 |
| FR | 2 871 572 A1 | 12/2005 |
| GB | 2012966 A | 8/1979 |
| GB | 2 206 969 A | 1/1989 |
| JP | 6-87861 U | 12/1994 |
| JP | 2007-205826 A | 8/2007 |
| JP | 20 2011 001 846 U1 | 6/2012 |
| WO | WO 2012/100938 A1 | 8/2012 |

* cited by examiner

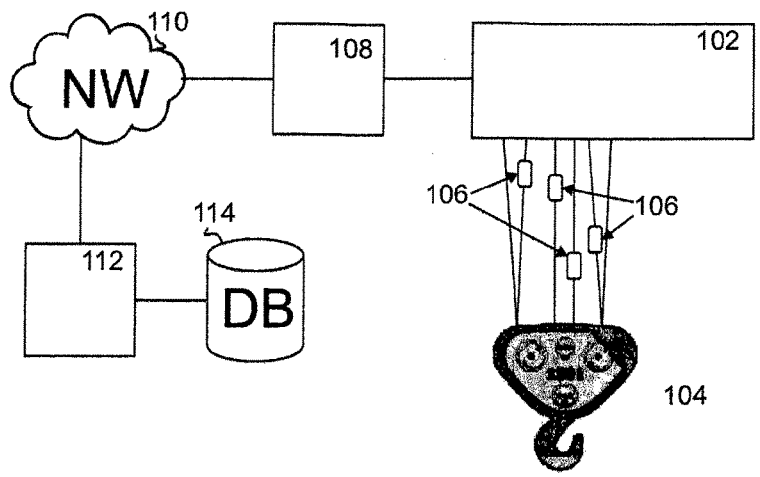
Figure 1
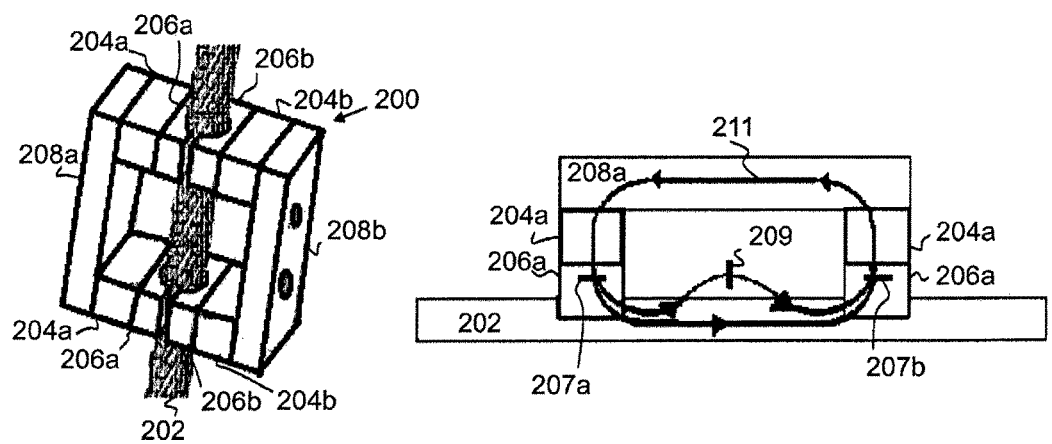
Figure 2a
Figure 2b
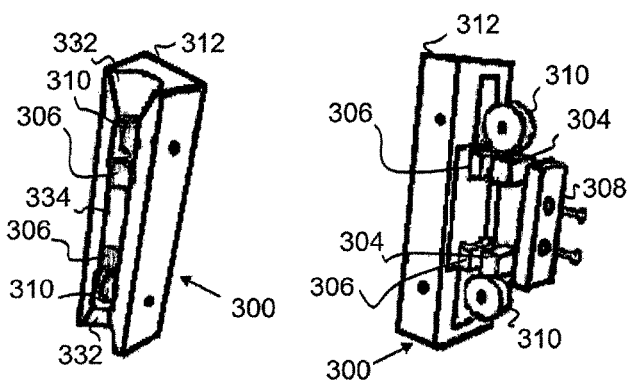
Figure 3a
Figure 3b

MONITORING CONDITION OF ELONGATED FERROUS OBJECT HAVING A LONGITUDINAL AXIS

FIELD

The present invention relates to monitoring condition of elongated ferrous objects, for example ropes, and particularly to monitoring, where a magnetic flux is guided through the object being monitored.

BACKGROUND

The following description of background art may include insights, discoveries, understandings or disclosures, or associations together with disclosures not known to the relevant art prior to the present invention but provided by the invention. Some such contributions of the invention may be specifically pointed out below, whereas other such contributions of the invention will be apparent from their context.

Ropes are typically used in cranes for hoisting cargo, for example containers. Ropes wear during use and their condition needs to be monitored to ensure their safety. Typical faults of ropes include Local Faults (LFs), where single wires are broken on the surface of the rope or inside the rope, and Loss of Metallic Area (LMA), where the diameter of the rope is reduced. A faulty rope may have an increased diameter by the surface of the rope being faulty. The diameter may be increased for example by dirt, a foreign object being attached to the rope, and/or loose strands or wires on the surface of the rope. In another example the rope may be faulty by a foreign object being attached to the rope, whereby the diameter of the rope may be increased.

Ropes may be monitored according to a maintenance program, where the condition of the ropes is regularly checked. During the maintenance of the ropes, they cannot be used and the crane is also out of operation. Accordingly, during the maintenance the operational efficiency, measured for example in operational time, is reduced for both the ropes and the crane. Still, the maintenance program that is once scheduled may be difficult or impossible to adjust to changes in the operation of the ropes. The ropes may be operated for example with higher loads and/or for longer periods than used for generating the maintenance program. These changes should be reflected in the maintenance program for example by increasing or decreasing the maintenance intervals in order to provide high operational efficiency.

Typically condition of ropes is checked by measuring each rope at a time over its whole length to determine the condition. Dedicated measurement instruments may be attached to the rope for the duration of the measurement and the maintenance personnel performing the measurements may also inspect the rope visually. After the measurements are performed, the instruments are detached from the rope and a next rope may be inspected. Accordingly, the typical checking of the condition takes time and requires highly qualified experts that are specialized in maintenance of the ropes. The availability of the experts and the measurement instruments to check the ropes of the cranes may also affect the scheduling of the rope maintenance, making the scheduling of the maintenance even more difficult, whereby high operational efficiency is even more difficult to achieve.

Accordingly, condition of the ropes is typically checked manually by instruments that are temporarily installed to the ropes by the service personnel. Typically these instruments check the condition of the rope by magnetically saturating the rope and measuring the magnetic flux inside and outside of the rope. These instruments fit tightly around the monitored rope to allow efficient transfer of the magnetic flux to and from the rope. However, the instruments have to be removed after the measurements have been performed so that the ropes and the crane may be operated for handling payload. If these instruments are not removed from the ropes, the instruments may travel attached to the rope to hoisting machinery and consequently result in seriously damaging the hoisting machinery and even dropping any payload carried by the ropes to the ground.

Consequently, the present instruments require manual work by maintenance personnel which introduces the possibility of human error and on the other hand since the present instruments cannot be used when the payload is being handled, monitoring the condition of the ropes requires scheduling of maintenance during which the crane is not used for handling payload.

SUMMARY

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Various embodiments of the invention comprise an apparatus, a monitoring arrangement, a method and a crane as defined in the independent claims. Further embodiments of the invention are disclosed in the dependent claims.

According to an aspect there is provided an apparatus for monitoring a condition of an elongated ferrous object having a longitudinal axis, said apparatus comprising two magnetizing circuits comprising magnetic poles arranged along the longitudinal axis, and a magnetic flux guide connecting the poles, said magnetizing circuits being arranged around the object at opposite sides along the longitudinal axis, wherein the magnetizing circuits are hinged together to be movable between a closed position, where the monitored object is enclosed between the poles of the magnetizing circuits and an open position, where monitored object is removable from the apparatus, the apparatus comprising an enforcing element operatively connected to the magnetizing circuits such that, in the closed position, the magnetizing circuits are pressed towards each other; wherein when the magnetizing circuits are pivoted from the closed position to the open position, the operative connection between the enforcing element and the magnetizing circuits is disconnected.

According to an aspect there is provided a monitoring arrangement of elongated ferrous objects, comprising an apparatus according to an aspect, and a sensor for measuring magnetic flux, said sensor being connected to the magnetizing circuits, and a controller connected to the sensor and configured to determine a movement of the magnetizing circuits from a closed position to an open position by a change, for example an interruption, of the magnetic flux.

According to an aspect there is provided a method by an apparatus or a monitoring arrangement according to an aspect, wherein the method comprises disconnecting the operative connection between the enforcing element and the magnetizing circuits by pivoting the magnetizing circuits from the closed position to the open position.

According to an aspect there is provided a payload handling apparatus, for example a crane comprising one or more ropes for hoisting payload and a monitoring arrangement according to an aspect, wherein an apparatus for monitoring a condition of an elongated ferrous object having a longitudinal axis according to an aspect is attached to the ropes, when payload is handled by the ropes.

According to an aspect there is provided a tool for disconnecting or connecting magnetizing circuits of an apparatus according to an aspect.

Some embodiments provide improvement comprising monitoring of elongated ferrous objects such as ropes, when they are being used, for example in payload handling. The monitoring provides that it is not necessary to schedule a specific maintenance to determine the condition of the elongated ferrous objects, but the monitoring may be performed continuously.

Some embodiments provide improved safety in monitoring ropes by disconnecting the magnetizing circuits from the monitored rope by pivotal movement of the magnetizing circuits with respect to each other into an open position. In this way the magnetizing circuits may be prevented from travelling attached to a faulty rope that has an increased diameter whereby damages to the rope, measurement equipment or other equipment may be prevented. Moreover, disconnection of the magnetizing circuits facilitates detecting, when the rope has an increased diameter, by changes in the measured magnetic flux.

In some embodiments, an open position of the magnetizing circuits includes angles, where the magnetizing circuits are separable at least by a diameter of the monitored rope to allow removal of the rope.

Some embodiments facilitate continuous monitoring of rope, preferably by magnetically saturating the rope, whereby changes in the condition of the rope may be measured during its use without separately scheduled maintenance breaks for inspecting the condition of the rope. The continuous monitoring of the rope facilitates immediately detecting, when the rope is faulty even without the rope having an increased diameter. On the other hand the continuous monitoring helps to avoid replacing the rope prematurely.

BRIEF DESCRIPTION OF THE DRAWINGS

In the following description, various embodiments are described by reference to the accompanying drawings, in which:

FIG. 1 illustrates a general architecture of arrangement for monitoring elongated ferrous objects having a longitudinal axis according to an embodiment;

FIG. 2a illustrates monitoring a condition of a longitudinal ferrous object having a longitudinal axis by an apparatus comprising magnetizing circuits, according to an embodiment;

FIG. 2b illustrates a side-view and a flow of magnetic flux between poles of one of the magnetizing circuits of FIG. 2a;

FIG. 3a illustrates a magnetizing circuit installed to an apparatus for monitoring a condition of an elongated ferrous object having a longitudinal axis, according to an embodiment;

FIG. 3b is an exploded view of the apparatus of FIG. 3a;

DETAILED DESCRIPTION

Figure 4A:
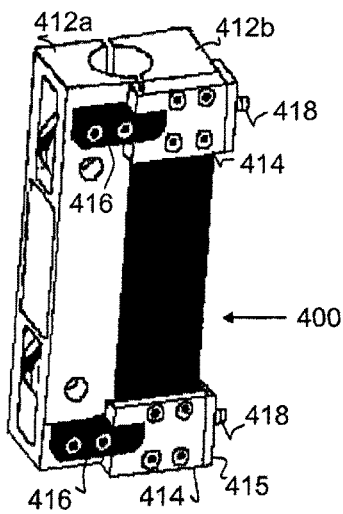
FIG. 4a illustrates an apparatus for monitoring a condition of an elongated ferrous object having a longitudinal axis, according to an embodiment.

In the following elongated ferrous objects are referred to as ropes made of iron or derived from iron. The presence of iron gives magnetic properties to the ropes such that the rope may be magnetised. Magnetic properties may be provided by using a ferrous material for the rope. Ferrous materials include ferrous metals such as mild steel, carbon steel, cast iron, and wrought iron. Most ferrous metals have magnetic properties, for example provided by the use of ferrite (a-Fe) in the metal alloy.

In various embodiments payload may refer to movable objects that are transported between physical locations on the ground, in buildings and/or in vehicles. The movable objects may be cargo transported by vehicles between an origin, for example a harbour, and a destination, for example a warehouse. In one example, the movable objects may be containers that have standardized dimensions and are conventional in transportation of goods by ships and trucks.

Examples of the elongated ferrous objects include but are not limited to objects such as a steel rod, tube, wire or wire rope. For purposes of description the term "rope" is used to refer to all of these structures. It is understood that the cross section of the rope can define a circular, curvilinear, rectangular, triangular, or faceted profile.

A typical rope is a linear collection of plies, yarns or strands which are wound together in order to combine them into a larger and stronger form. Materials suitable for the ropes include but are not limited to steel and pig iron (with a carbon content of a few percentage) and alloys of iron with other metals. Also other materials may be used provided they can be magnetized to allow a flow of magnetic flux within the material. Also requirements regarding the practical implementations of the ropes should be considered, such as the strain the ropes have to endure.

FIG. 1 illustrates a general architecture of monitoring arrangement of ropes according to an embodiment. The rope monitoring arrangement includes one or more apparatuses 106 for monitoring a condition of the ropes. The apparatuses have magnetizing circuits that generate a magnetic flux between magnetic poles. The apparatuses are installed to the ropes such that the rope may be subjected to the generated magnetic flux and the rope is saturated by the magnetic flux. Consequently, the rope is saturated along its length between the poles. The generated magnetic flux flows between the poles through the rope. The apparatuses include sensors that may measure the magnetic flux entering and/or leaving the rope. Also other sensors may be provided as is illustrated in FIG. 2b.

Referring back to FIG. 1, the ropes may be attached to a supporting structure 102, whereby payload and payload handling equipment 104, for example hooks, may be attached to the ropes to be supported by the ropes so that the payload may be handled, e.g. hoisted or lowered by the rope. The ropes may be attached to the supporting structure such that they are movable, for example by hoisting. Hoisting machinery may be used to provide the hoisting by installing the ropes to the hoisting machinery.

A controller 108 may be connected to the apparatuses installed to the ropes. The controller may be directly connected to the apparatuses or connected via the supporting structure. A direct connection between the controller and apparatus may be an electrical connection implemented for example by a data bus for example Industry Standard Architecture (ISA) or Peripheral Component Interconnect (PCI) bus used in computers, when the controller is implemented within the apparatuses. The controller may be a computer or a processing unit including logic circuitry and memory, for example. In one example, the controller may be a Programmable Logic Controller PLC as is conventional in cranes. In cranes, the PLC connects to the crane functions, for example the hoisting machinery. An industrial bus, for example Profibus (Process Field Bus) and CANopen, may be used for connecting the PLC and the crane functions. The memory may be a volatile or a non-volatile memory, for example EEPROM, ROM, PROM, RAM, DRAM, SRAM, firmware, programmable logic, etc.

Accordingly, in one example the apparatuses installed to the ropes may be connected to the controller via a connection to an industrial bus provided at the supporting structure. The connection between the apparatuses installed to the ropes and the supporting structure may be provided by a wireless or wired connection (not shown). A wireless connection may be provided by information communicated on a radio frequency band by a transmitter and a receiver employing corresponding protocols that allow the transfer of the information between them. In one example a wireless connection may be implemented by a Wireless Local Area Network connection according to the IEEE 802.11 family of specifications.

A wired connection may be implemented by electrical wiring that connects to the industrial bus in the supporting structure via an adaptor. The electrical wiring and communications protocols may be implementation specific. In one example, the electrical wiring may be implemented as an industrial bus connection.

The apparatuses installed to the ropes may operate at least as transmitters to allow transfer of measurement information to a receiver located at the supporting structure. However, it is possible that the connection between the supporting structure and the apparatuses installed to the ropes is bidirectional and both ends of the connection operate as transmitters and receivers, i.e. transceivers.

Accordingly, in one example, a wired connection provided by an industrial bus may be used between the supporting structure, e.g. the hoisting machinery, and the controller, and a wireless connection may be used between the supporting structure and a monitoring apparatus attached to the ropes.

The controller may connect to a service centre 112 over a network 110. The network may be a wide area network including one or more access networks that may provide wired or wireless access to the network. The wireless access networks may be implemented by the WLAN or by mobile communications networks defined by the $3^{rd}$ Generation Partnership Project, for example, Global System for Mobile Communications, Terrestrial Trunked Radio Access, Universal Mobile Telecommunications System, Long Term Evolution and LTE-Advanced. Wired access may be provided over Ethernet connections. Internet Protocol version 4 or 6 may be used in addressing in the communications.

The controller and the service centre may be equipped with adapters that provide the communications capabilities on the connections. In one example, the adapters for wireless communications include modems that operate according to the above-mentioned communications standards. Adapters for wired connections may include bus cards connect to internal buses and thereby provide wired connectivity to hardware and/or software platforms of the described entities.

The service centre may be connected to a data storage 114 that stores information of installed ropes. The stored information may comprise information identifying the ropes and include information on condition of the ropes. The ropes may be identified by the crane and/or crane functionality they are installed to, for example. The condition may be specified as a time period until maintenance is to be performed and/or as a level of the condition. Different condition levels may be: excellent, good, needs maintenance and damaged. Each level may be specified by one or more thresholds for determining which condition matches the measurements received from the rope. The controller may process the measurement information from the ropes and determine the condition and/or the time period until maintenance should be performed. It is also possible that the service centre receives the measurement information from the ropes via the controller and the service centre determines the condition and/or the time period until maintenance should be performed. The data storage may be internal to the service centre or external to the service centre. The service center may be implemented as a computer including an internal bus that connects to the data storage via the bus. In another example the data storage resides in a server external to the service centre and the data storage may be connected over a wired or wireless connection that may be implemented according to the communications standards described above.

Preferably the apparatuses installed to the ropes allow movement of the ropes as they are hoisted. In one example the apparatus in installed around a rope that is monitored by the apparatus. Accordingly, as the rope is hoisted, it moves through the apparatus installed around the rope. In this way the apparatus may measure the rope through the whole length of the rope as the rope is hoisted. To allow the movement, the apparatus has a passage that allows movement of the rope in the hoisting direction. In a typical deployment scenario, where the ropes are hoisted in a vertical direction, for example in lifting payload or lowering payload to the ground, the apparatuses installed to the ropes may be supported to the supporting structure by cabling to suspend them at a suitable position with respect to the rope. This may be desirable for practical reasons to keep the apparatus from sliding to the hook, for example. On the other hand it is possible that the apparatus is integrated to the hook or other structure, where the rope is passed through, and no cabling is needed to support the apparatus. However, whether support is needed or not and how the support is implemented relates to details that need not to be discussed herein to avoid obscuring the description with too much details.

FIG. 2a illustrates monitoring a condition of a rope 202 by an apparatus 200 comprising magnetizing circuits according to an embodiment. The magnetizing circuits are illustrated in their closed position around the rope. In the closed position the magnetizing circuits form a passage for the rope to travel between the magnetizing circuits. Accordingly, the diameter of the passage is larger than the diameter of the rope. The apparatus may be used to implement an apparatus installed around the ropes described in a rope monitoring arrangement of FIG. 1. In FIG. 2a, two magnetizing circuits are arranged around the rope. Each of the magnetizing circuits includes two poles 204a, 204b that are arranged along the longitudinal axis of the rope. The poles magnetically saturate the rope, whereby a magnetic flux flows in the rope, along the length of the rope, between the poles of both magnetizing circuits. The magnetic poles may be provided by permanent magnets or by electromagnets, such that a magnetic flux is generated, as is well-known to a skilled person and therefore, this does not need to be discussed further herein.

The poles of each magnetizing circuit are connected by magnetic flux guides 208a, 208b that guide the magnetic flux between the poles. Accordingly, the magnetic flux guides guide the magnetic flux between the poles outside the rope. FIG. 2b illustrates a side-view and an exemplary flow path 211 of the magnetic flux between poles of one of the magnetizing circuits of FIG. 2a. Preferably the magnetic flux introduced by both magnetizing circuits to the rope is substantially the same.

Pole shoes 206a, 206b are arranged between the poles and the rope. The pole shoes guide the magnetic flux between each of the poles and the rope. In this way the magnetic flux leaving the poles may be concentrated to the rope as well as the magnetic flux leaving the rope may be concentrated to the poles.

The magnetizing circuits are arranged on opposite sides of the rope. The pole shoes are arranged at a distance from the rope such that the magnetic flux may flow between the rope and each of the pole shoes. Accordingly, the pole shoes define a passage for the rope as the rope moves through the magnetizing circuits. Preferably the pole shoes are designed to a constant distance from the rope, thereby following the shape of the rope passing the magnetizing circuits. Accordingly, the cross section of the apparatus, when the magnetizing circuits are closed around the rope, matches substantially the cross-section of the rope, at the side of the magnetizing circuits that meet the rope.

The magnetizing circuits arranged around the rope may be the same and made of a ferrous material. The magnetizing circuits may be implemented in opposite halves of a structure, for example in pieces of alloy bodies or any non-ferrous material that house the magnetizing circuits. It is also possible to implement the magnetizing circuits without a separate housing structure, whereby the air surrounding the magnetizing circuits may serve the purpose of the housing by magnetically isolating the magnetizing circuits.

The magnetizing circuits may include one or more sensors 207a, 207b, 209 for measuring the magnetic flux. The sensors may be installed to each of the poles to measure the magnetic flux leaving one pole towards the rope and to measure the magnetic flux received at the other pole from the rope. In this way the magnetization of the rope may be measured. The measured magnetization of the rope may be used to determine the condition of the rope. Variations of the magnetization may indicate a faulty rope, one or more foreign objects being attached to the rope and/or a fault in the measurement equipment. The faulty rope may comprise a rope with increased diameter and/or a decreased diameter as described above. It may also be possible to detect faulty ropes even if their diameter is not reduced or increased.

One or more sensors 209 may be installed between the poles in the longitudinal direction of the rope. In this way the magnetic flux may be measured that has leaked outside the rope. This may happen, when the rope is faulty.

The magnetic flux may be measured by its magnitude. The magnitude may be indicated by analogue or digital signals. The signals may be electrical signals that have voltages that correspond to the measured magnitudes of the magnetic flux.

FIG. 3a illustrates a magnetizing circuit installed to an apparatus 300 for monitoring a condition of rope, according to an embodiment. FIG. 3b is an exploded view of the apparatus of FIG. 3a. The magnetizing circuit may be constructed as described in FIG. 2a. The magnetizing circuit in FIGS. 3a and 3b includes poles 304, pole shoes 306 and a magnetic flux guide 308 that correspond to the poles 204a, 204b, pole shoes 206a, 206b and magnetic flux guides 208a, 208b illustrated in FIG. 2a. The magnetizing circuit is installed to a body 312 that is preferably of non-ferrous material. In this way the magnetic flux between the poles may be concentrated to flow via the rope and the flux guide with minimal deflections to the body. Rollers 310 are installed to both ends of the body. The rollers provide positioning of the rope with respect to the poles that are between the rollers in the longitudinal direction of the rope. The rollers are rotated by the rope moving between the magnetizing circuits. Also other guiding means may be used than rollers, for example guiding means that slide the rope to the desired position. However, since the rollers rotate with the rope passing between them, their friction to the rope is less than that of the guiding means that slide along the rope.

FIG. 4a illustrates an apparatus 400 for monitoring a condition of rope, according to an embodiment. The apparatus may be used to implement an apparatus installed to the ropes described in a rope monitoring arrangement of FIG. 1. The apparatus includes two magnetizing circuits that are arranged around the rope. The magnetizing circuits are installed into bodies 412a, 412b that form opposite halves of the apparatus 400. The apparatus 300 of FIGS. 3a and 3b may be used to implement the opposite halves. FIGS. 2a and 2b illustrate the arrangement of the magnetizing circuits around the rope. Accordingly, in FIG. 4a the halves are symmetrically arranged around the rope. In this way, the magnetic flux may be guided to the rope symmetrically around the circumference of the rope and both sides of the rope may be measured with the same accuracy. It should be appreciated that in some implementations it may be sufficient to apply different monitoring to different sides of the rope, whereby non-symmetrical arrangements may be preferred over symmetrical arrangements.

Figure 4B:
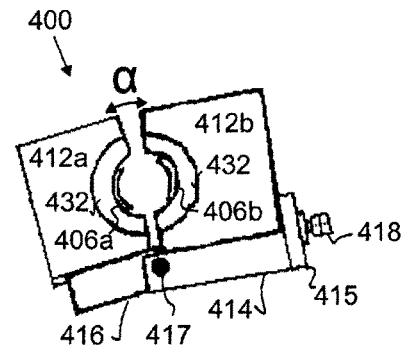
FIG. 4b illustrates the apparatus of FIG. 4a as viewed from its end, where the elongated ferrous object enters the apparatus.

FIG. 4b illustrates the apparatus of FIG. 4a as viewed from its end, where the rope enters the apparatus. In the view from the end, pole shoes 406a, 406b of the two magnetizing circuits are visible. In this example the pole shoes are positioned in the bodies such that they are arranged opposite to each other, i.e. symmetrically, around the rope, when the apparatus is installed to the rope. A passage for the rope is formed by the space between the opposite body halves. The passage allows movement of the rope in the hoisting direction of the rope. Accordingly, the distance between the body halves for example measured at the opposite pole shoes, is preferably greater than the diameter of the rope. Rollers may be installed to the body halves as illustrated in FIGS. 3a and 3b. The rope enters the passage between the magnetizing circuits as guided by the rollers. The respective distance of the rollers in opposite body halves and the position of the rollers with respect to the pole shoes may be used to position the rope at the desired distance from the pole shoes of the opposite body halves.

Referring back to FIGS. 4a and 4b, the bodies 412a, 412b connect the magnetizing circuits by hinging them movable between a closed position, where the object is enclosed between the poles of the magnetizing circuits and an open position, where the magnetizing circuits are at an angle that allows removal of the object. The specific angle may be determined on the basis of the dimensions of the monitored ropes. Preferably the angle α between the magnetizing circuits in the closed position is smaller than an angle allowing removal of the object in the open position. The angle may be measured as an angle between the bodies.

The angle, where the bodies and the magnetizing circuits move from the closed position to the open position, may be used to design the dimensions of the parts of the apparatus, for example the cam, to allow a sufficient opening in the open position of the magnetizing circuits, so as to enable removal of the rope. It should be appreciated that the angle at which the bodies and the magnetizing circuits move from the closed position to the open position may not be big enough to allow removal of the rope, but the angle where the removal is possible is greater than the angle, where the position is changed from the closed position to the open position. Accordingly, in the open position the bodies may have a plurality of angles over a range of angles, where only the highest angles of the range allow removal of the rope. The angle, where the rope may be removed allows also insertion of the rope between the bodies and the magnetizing circuits.

In an embodiment, a closed position may be defined as a position of the bodies around the rope, where an angle between the bodies is substantially zero. With such an angle, the pole shoes of the bodies are at the same distance from the monitored rope between the bodies. In this way, the pole shoes guide the magnetic flux uniformly to the rope.

In an embodiment, an open position may be defined as a position of the bodies around the rope, where the bodies are angled with respect to each other. Thereby, an angle between the bodies is greater than zero. In the open position, the magnetic flux from the pole shoes is diverted from the rope. Opposite pole shoes of the opposite magnetizing circuits are also hinged with respect to each other, whereby the magnetic flux is guided non-uniformly to the rope.

The hinging may be provided by a hinging mechanism that includes a cam 416 and an enforcing element 414. The cam and the enforcing element may be fixed to different bodies 412a, 412b and hinged together by a pin 417. In this way the bodies are movable around the pin that hinges the cam and the spring element together.

In the closed position, the enforcing element exerts a force to the cam for moving the magnetizing circuits towards their closed position. Accordingly, the force presses the bodies against each other and towards a zero angle between the bodies.

The enforcing element may be implemented by a spring element, a storage of potential energy, a pneumatic circuit and/or a hydraulic circuit. Accordingly, also a combination of the enforcing elements may be used. The potential energy may be stored in a spring element, a pneumatic accumulator or a hydraulic accumulator or a weight movable along a passage extending in the direction of the gravity. Although, the embodiments herein are described using the spring element, a skilled person understands also the other spring elements described herein may be used to exert a force to the cam.

The spring element may comprise one or more springs that operate between the cam 416 and a plate 415 that supports the springs within the spring element. An adjustment nut 418 may be installed to the plate to communicate with the springs within the spring element. The rotation of the nut may be communicated through the plate such that an initial compression of the springs in the spring element may be adjusted, for example increased or decreased.

It should be appreciated that the apparatus for monitoring the ropes may include one or more hinging mechanisms illustrated in FIG. 4b, for example two as in FIG. 4a, but also one, three, four or any number of hinging mechanisms.

It should be appreciated that a hinging mechanism may include two or more parallel axes around which the bodies may be pivoted. The axes are preferably substantially in the same direction. In this way the angle between the bodies in the position may include an angle formed by pivoting the bodies around more than one axis and a greater opening angle between the bodies may be provided.

The axes may be implemented by corresponding pins 417. The bodies connected by the pins may be turned around the pins and/or supported for pivotal movement by the pins. The hinging mechanism may include more than one pin, for example two or more pins, that are positioned parallel to each other and substantially in the same direction. When a hinging mechanism has two parallel pins, the parallel pins are preferably separated by a distance of 0.2-2× the diameter of the rope.

A connecting member may be positioned between the parallel pins to allow pivotal movement of bodies as well as the pins with respect to each other. The connecting member is arranged between the pins such that the bodies connected by the hinging mechanism are allowed to turn between the open position and the closed position by pivoting the bodies around the axes formed by the pins. A similar structure of two parallel pins connected by a hinging mechanism is known from hinges used in suit cases or violin cases having thick walls, whereby a larger opening angle is practical to have. A hinging mechanism with more than two pins may be provided by arranging a connecting member between each pair of parallel as explained above.

The force exerted on the cam by the spring element is preferably adjusted such that a faulty rope that enters the passage between the bodies causes movement of the bodies with respect to each other and in consequence an increase of the angle between the bodies. The bodies move from the closed position to the open position, when the angle increases above a threshold angle. The threshold may be designed depending on each implementation for example to match different rope diameters. It should be appreciated that, when the rope is moving through the passage, for example during payload handling, and the rope is magnetically saturated, the magnetic circuits are drawn towards the rope and towards the closed position. Thereby, the force exerted by the spring element may be adjusted to take into account this force such that the magnetizing circuits are opened, when the rope is moved between the magnetizing circuits and being saturated. Accordingly, the force exerted by the spring element is preferably adjusted such that the bodies move from the closed position to the open position in case the diameter of the rope is increased beyond its specified diameter.

In an embodiment, a faulty rope, for example a rope having an increased diameter, that enters between magnetizing circuits in a closed position, exerts a force to the magnetizing circuits, whereby the magnetizing circuits are moved from the closed position towards the open position. Accordingly, the force from the rope exceeds the force communicated from the spring element to the magnetizing circuits and/or a magnetic force exerted by the magnetizing circuits to the rope. It should be appreciated that the magnetic force may be omitted in considering the implementation, when the magnetic force is relatively small compared to the force exerted by the spring element.

Figure 4C:
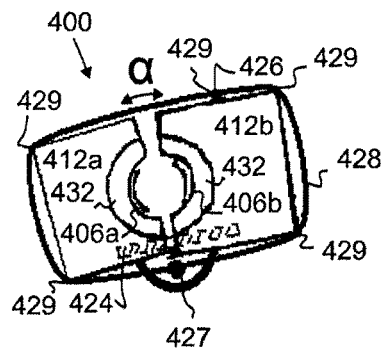
FIG. 4c illustrates an example of hinging mechanism as viewed in the apparatus of FIG. 4a from its end, where the elongated ferrous object enters the apparatus.

FIG. 4c illustrates an example of hinging mechanism as viewed in the apparatus of FIG. 4a from its end, where the elongated ferrous object enters the apparatus. The hinging mechanism distributes the functionality of the enforcing element to a spring element 424 and a band 428 around the bodies, whereby the band supports the bodies to the closed position and the spring element pushes the bodies towards the open position. The spring element may comprise a spring element, one or more coil springs, disc springs, a storage of potential energy, a pneumatic circuit and/or a hydraulic circuit, or their combination. A pin 427 hinges the bodies 412a, 412b together to be movable between the open position and the closed position by pivotal movement around the pin similar to in FIG. 4b. More than one band, for example, two, three, four or any number of bands may be used. The band may be made of metal, for example stainless steel or plastic material. Preferred properties of the material for the band should include durability against low temperatures, high temperatures, Ultra Violet radiation, corrosion, oil and/or grease. The bodies may be moved from the closed position to the open position by a faulty rope having an increased diameter entering the passage between the bodies similar to the example of FIG. 4b. Since the diameter of the rope is enlarged, the rope is pressed against the walls of the passage causing the bodies to pivot around the pin towards the open position. The pivoting of the bodies causes a force towards the band that supports the bodies in the closed position. When the force pressing against the band is sufficiently large, the band breaks in at least one breaking point 429 and the bodies are moved to the open position. Since no longer being supported by the band, the bodies are maintained in the open position. The band may be fixed to the bodies such that it does not fall off when breaking. When fixing a band or multiple bands around the bodies, a specific tool can be provided. For the tool is essential that it pulls the band/bands in a uniform tension. Uniform tension makes it possible to control a force that is needed to open the bodies.

The breaking point may comprise a forced breaking point (Sollbruchstelle) that is designed to break, when it is exposed to a predetermined amount of stress caused by pivoting of the bodies. The breaking point of the band may be in a corner or corners of the body halves or some other part of the band. In one example, the breakage of breaking point may be provided by a cutting edge 426 that is pressed against the breaking point, when the bodies are pivoted towards the open position. Thereby, the breaking point may be defined by the location of the cutting edge. It should be appreciated that the band may not break immediately upon pivoting of the bodies but the band may be designed to break at a specific angle of pivoting of the bodies.

In an embodiment, the band illustrated in FIG. 4c may be arranged around the bodies of FIG. 4b that are hinged by the hinging mechanism including the cam 416. The breaking point of the band may be adjusted to break even before the bodies are moved from the closed position to the open position by the co-operation of the cam and the enforcing element. In this way, the broken band may be used indicate smaller faults of the rope that are not sufficient to move the bodies to the open position, but only to break the band.

Figure 5:
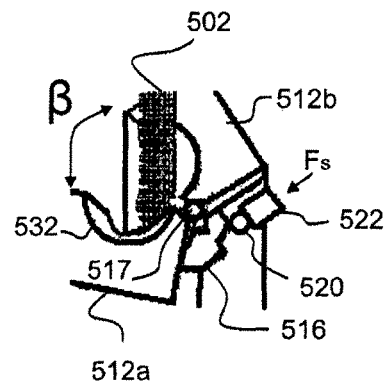
FIG. 5 illustrates communications between a cam and an enforcing element in a hinging mechanism according to an embodiment.

FIG. 5 illustrates communications between a cam and a spring element in a hinging mechanism according to an embodiment. The apparatus may be the apparatus described in FIG. 4a, where a rope 502 is positioned between the body halves 412a, 412b, 512a, 512b. The hinging mechanism includes a pin 517, a cam 516 and a spring element 522 which correspond to the pin 417, a cam 416 and a spring element 414 described above with FIG. 4a.

In the illustration of FIG. 5, the spring element may comprise one or more springs. The springs may be disc springs that are arranged in series to provide a combined spring force of all the disc springs. Accordingly, the number of disc springs may be selected to provide a suitable minimum and maximum spring force from the springs. Also coil springs may be used. A rotatable part 520 is installed to the end of the spring element towards the cam. The springs, rotatable part and the pin may be enclosed within a cover plate for protection against dirt. The cover plate may be penetrated by the pin, when the cover plate is assembled.

The cam includes two surfaces for receiving the force exerted by the springs. The two surfaces form the head of the cam towards the spring element in FIG. 5. The two surfaces are also illustrated in the FIGS. 6a and 6b by items 623 and 625. The surfaces are inclined away from the spring element to the operating direction of the spring element $F_s$. In this way the force exerted by the spring element is received by the rotatable part that communicates the force to one of the inclined surfaces of the cam.

The rotatable part 520 provides the spring element and the cam being movable with respect to each other. The rotatable part moves on the surfaces that receive the force exerted by the spring element in different locations along the surfaces. In one example the rotatable part operates as a bearing between the cam and the spring element. The spring element is fixed to the rotatable part such that the rotatable part is rotatable against the cam.

In a closed position and open position of the bodies 512a, 512b different surfaces of the cam receive the force from the spring element. When the bodies are in the closed position, the surface that is closest to the body, in which the spring element is fixed, receives the spring force and when the bodies are in the open position, the other surface receives the spring force.

The spring element 522 and the cam 516 may be fixed to different bodies 512a, 512b of the apparatus. In FIG. 5, the magnetizing circuits of the apparatus are shown in their open position, where the angle β between opposite body halves 512a, 512b that correspond to body halves 412a and 412b on FIGS. 4a and 4b, allows removal of the rope 502.

When the bodies are in the closed position, a movement of the bodies towards an open position is communicated to the spring element by the cam via the rotatable part 520 that is moved on the surface of the cam closest to the body 512b, where the spring element is fixed. The surface of the cam is inclined to the operating direction $F_s$ of the spring element and away from the springs. Preferably the inclination is towards a direction of increased force from the spring towards the cam, as the body halves are turned towards their open position. In this way the force exerted from the spring element increases as the bodies are opened.

As the body halves are turned towards the open position, the rotatable part is moved on the surface of the cam. Once the bodies are opened to an angle β, where the rotatable part has moved to the end of the surface, the rotatable part has reached a tip of the cam formed by a connection of the inclined surfaces. When the bodies are opened to a wider angle β, the rotatable part moves to the other inclined surface, and the bodies are in the open position. Now in the open position the spring force received by the inclined surface of the cam closest to the body in the closed position is decreased, as it no longer receives the spring force or the force is substantially lower.

Then in the open position, the spring force is received by the surface of the cam that is inclined to the opposite direction than the surface of the cam that received the spring force in the closed position. The inclined surfaces of the cam form a tip towards the spring element. In this way the maximum displacement of the spring element, and thereby the maximum force of the spring element is achieved at the tip, as the body halves are moved between the closed position to the open position. When the bodies are opened or closed, the movement towards a different position is always "uphill" as the rotatable part crosses the tip only when the springs of the spring element are sufficiently displaced. On the other hand the movement towards an open position when already in the open position is "downhill" since this movement allows extension of the springs.

Accordingly, in various embodiments the length of the inclined surface closest to the body fixed to the spring element may be chosen such that the maximum compression of the springs at the tip inclined surfaces results in a desirable force needed for moving the bodies from a closed position to an open position. The desirable force may be determined on the basis of the angle at which the body halve are moved from the closed position to the open position. At this angle, the force exerted by the spring element to the body halves and the magnetic force drawing the body halves towards the rope, and the closed position, is exceeded by the force of the rope between the bodies pushing the bodies towards the open position.

When ropes are monitored by an apparatus according to various embodiments installed to a rope, faulty portions of the rope may enter the apparatus. When the diameter of the rope is increased from an original diameter of the rope, the rope impacts the apparatus. A mouth of the passage that receives the rope may be shaped for softening the impact as is described below. The bodies are hinged together and thereby movable apart. The impact of the faulty portion is received by the walls of the passage causing a force being transferred by the cam to the spring element. The cam has two surfaces that communicate with the spring element. The surfaces are movable with respect to the spring element to receive the force exerted by the spring element in different locations along the surfaces. One of the surfaces extends in a direction of increasing force from the spring being communicated to the surface by the movement of the surface with respect to the spring element and up to a length of the surface, where the magnetizing circuits are moved from a closed position to an open position and the spring force received by the surface is decreased.

In various embodiments including magnetizing circuits installed to body halves, for example in FIGS. 3a, 4b, 4c and 5, a passage for a rope may be formed by space between the opposite body halves. The passage may have ends 332, 432, 532 with a larger diameter than the mid-portion of the passage between the ends. The mid-portion 334 may be dimensioned according to the diameter of the measured rope to allow the rope to travel through the body halves. The ends of the passage provide that a faulty rope having an increased diameter is increasingly pressed against the walls of the passage, and a rope having diameter larger than the diameter of the mid-portion of the passage may enter the passage and cause opening of the body halves. More specifically, it is the force that is perpendicular to the axis of the rope that is communicated from the rope to the walls of the passage to cause the opening of the body halves, as the faulty portion of the rope enters the passage. When the force received from the rope entering to the passage is sufficiently large, the bodies are moved from their closed position to the open position as described in various embodiments herein. In one example the ends of the bodies are cone shaped such that the diameter of the passage is the largest at the mouth of the passage and is decreased towards the mid-portion. Conical, trumpet mouthed or similar shapes can be used to provide the ends. In this way an increasing force may be received from a faulty portion of the rope to the passage walls, when the rope enters the passage and travels towards the mid-portion. The exact dimensions of the cone shaped ends may be designed depending on rope type and diameter. Further examples of mechanisms for moving the magnetizing circuits from their closed position to the open position are described below, for example with reference to FIGS. 10 to 13.

In an embodiment, the spring element and the cam are fixed to different magnetizing circuits that are hinged together. The cam and the spring element are dimensioned with respect to each other such that a sufficient torque of the cam around its pivoting point moves the magnetizing circuits from a closed position to an open position to provide disconnection of the magnetizing circuits. In this way the magnetizing circuits may be detached and removed from the rope to avoid the magnetizing circuits from travelling with the rope. Accordingly, the disconnection of the magnetizing circuits may indicate a faulty rope, e.g. an increased diameter of the rope.

It should be appreciated that already a single surface of the cam that is movable with respect to the spring element may provide opening of the magnetizing circuits. Thereby, it is possible to omit further surfaces of the cam that receive force from the spring element.

However, when different surfaces of the cam receive force from the spring element in the open position and the closed position, closing and opening of the body halves is provided, while continuously receiving spring force by on the surfaces of the cam. Using inclined surfaces the change between the closed position and the open position is then always towards the direction, where the spring element resists the movement.

Figure 6A:
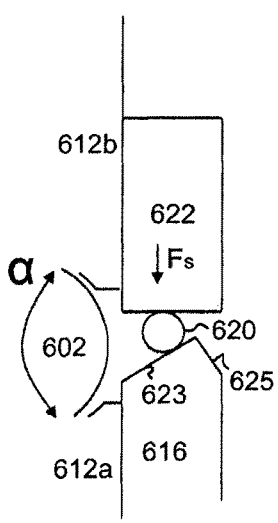
FIG. 6a illustrates magnetizing circuits in their closed position and FIG. 6b illustrates the magnetizing circuits of FIG. 6a in their open position, according to an embodiment.
Figure 6B:
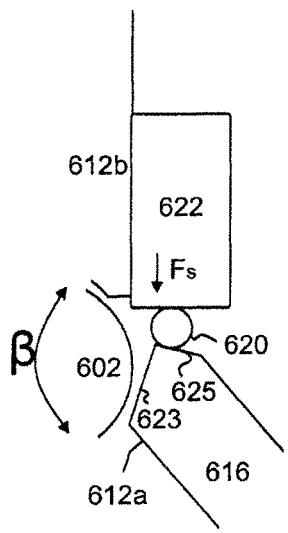

FIG. 6a illustrates magnetizing circuits 612a, 612b in their closed position and FIG. 6b illustrates the magnetizing circuits of FIG. 6a in their open position, according to an embodiment. The magnetizing circuits may be arranged into body structures as described in the above embodiments, for example in FIGS. 3a and 3b. In the closed position, the angle α between the body structures is substantially zero and smaller than the angle of the body structures in the open position similar to explained with FIGS. 4a and 4b. A spring element 622 may be fixed to one of the magnetizing circuits 612b and a cam 616 may be fixed to the other magnetizing circuit 612a. A rotatable part 620 is arranged between the cam and the spring element. Depending on the implementation of the attachment of the rotatable part to the spring element, the rotatable part may be positioned for example partly within the spring element. The rotatable part may be attached to the spring element and to touch a surface 623, 625 of the cam such that it may be engaged in a rotational movement by the cam when the magnetizing circuits are pivoted between the closed and open positions. In this way the rotatable part is rotated by the cam. The pivoting of the magnetizing circuits may be provided by a hinge mechanism as described above.

In FIG. 6a, in the closed position of the magnetizing circuits, a rope 602 may be between the magnetizing circuits to allow monitoring of the rope by magnetic flux being guided through the rope. In the closed position the magnetizing circuits may be around the rope. The magnetizing circuits may be maintained around the rope by the force exerted by the spring element to the cam, whereby the magnetizing circuits are pressed towards each other to enclose the rope between them. Preferably the cam has an inclined surface 623 that receives the force from the spring when the magnetizing circuits are in their closed position. The inclination of the surface provides that the surface is inclined inwards and towards the magnetizing circuits. Accordingly, the inclination diverts the surface from being perpendicular to a direction of force $F_s$ of the spring element acting on the rotatable part. In this way the surface is inclined away from the spring element and towards magnetizing circuits. Movement of the cam and the spring element, when the magnetizing circuits are opened, their position changes with respect to each other. When their position with respect to each other is changed, the rotatable part moves "uphill" on the inclined surface 623 of the cam. This causes compression of the spring element and an increased force is exerted from the spring to the cam. The force is increased until the magnetizing circuits are pivoted to an angle 3 with respect to each other, where the rotatable part has reached the end of the inclined surface. When the magnetizing circuits move beyond this angle, they are in the open position described in FIG. 6b.

In FIG. 6b the magnetizing circuits are maintained in the open position by the force exerted by the spring to the cam. In the open position, the angle β between the body structures is greater than the angle α in the open position of the body structures. The spring element now exerts a force to the cam to a surface 625 of the cam that is inclined away from the spring element. The surface is located at the side of the cam away from the magnetizing circuits. Accordingly, in the open position the surface of the cam that acts with the rotatable part is inclined outwards and away from the magnetizing circuits. Accordingly, the inclination diverts the surface from being perpendicular to the direction of force $F_s$ of the spring element acting on the rotatable part. Thereby, movement of the magnetizing circuits to greater angles with respect to each other, i.e. moving them more apart, moves the rotatable part now "downhill" on the inclined surface in the open position. In the "downhill" direction the force received by the cam from spring is reduced. The "downhill" direction of the inclined surface provides that the magnetizing circuits are opened quickly after the magnetizing circuits are pivoted to the angle 3.

In FIGS. 6a and 6b, the surfaces may be implemented as linear or spline formed, for example.

Figure 7:
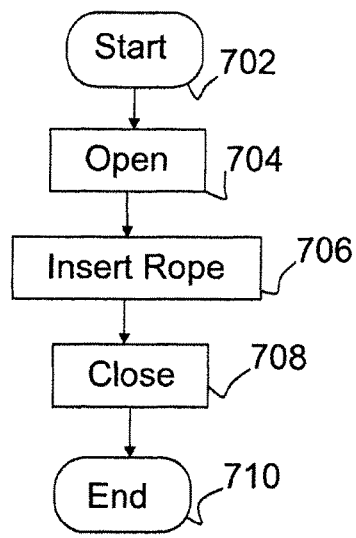
FIG. 7 illustrates a method by an apparatus according to an embodiment.

FIG. 7 illustrates a method by an apparatus according to an embodiment. The apparatus may be the apparatus described in FIG. 4a. The apparatus may be installed as a part of a rope monitoring arrangement of FIG. 1, whereby the method may involve the rope monitoring arrangement. The method may be performed by the apparatus described in an embodiment, a rope monitoring arrangement including the apparatus or by service personnel installing the apparatus or the rope monitoring arrangement to monitor ropes, for example in a crane. The method may start 702, when a rope that fits between the magnetizing circuits in their closed position is provided. The dimensions of the apparatus may be selected such that the provided rope may be moved between the magnetizing circuits. The rope is movable between magnetizing circuits such that the different sections of the rope along its length may be inspected by the apparatus as the rope is moved for example in handling payload.

The method comprises moving 704 the magnetizing circuits into the open position. This may be performed by a tool that forces the magnetizing circuits separate, although being pressed against each other by the spring element. It is conceivable that a special rope having a locally variable diameter may be lead through the magnetizing circuits such that the magnetizing circuits are opened by a section of the rope with a sufficiently large diameter of the rope forcing the magnetizing circuits to an open position, when the special rope is moved through the magnetizing circuits. For opening the magnetizing circuits by the special rope, a passage for the rope between the magnetizing circuits may have ends 332, 432, 532 with a larger diameter than the mid-portion of the passage between the ends, as described above in FIGS. 3a, 4b, 4c and 5. However, also electrical motors, pneumatic or hydraulic pumps may be connected to the magnetizing circuits or the body structures including the magnetizing circuits and controlled to drive the magnetizing circuits from the closed position to the open position or from the open position to the closed position. The electrical, hydraulic, pneumatic or mechanic devices are particularly preferred in case of thick and heavy ropes.

In 706, the rope to be monitored is positioned between the magnetizing circuits. The rope may be placed between the poles of the other magnetizing circuits according to FIG. 2b. When the variable diameter rope is used, the part of the rope fitting between the magnetizing circuits in the closed position is placed between the poles.

In 708, the magnetizing circuits are moved to the closed position. In the closed position both the poles of the magnetizing circuits are positioned to the rope according to FIG. 2b. This phase may be performed manually or as driven by the electric or hydraulic systems. A tool for manually opening and/or closing the magnetizing circuits is provided below.

In 710 the rope is positioned between the magnetizing circuits and it may be magnetized for monitoring the condition of the rope. Preferably the rope is magnetically saturated by the magnetizing circuits. The condition of the rope may be monitored by sensors that measure the magnetic flux entering and leaving the rope and the magnetic flux that leaks outside of the rope. The sensors may be arranged for example according to FIG. 2b. When the rope is positioned between the magnetizing circuits, the rope is preferably moved through the magnetizing circuits so that the condition of the rope may be measured from various parts of the rope, preferably from the whole length of the rope. Typically, the rope may be moved by hoisting machinery, as is typical in cranes. The measurements may be used to determine when the magnetizing circuits are moved from a closed position to an open position by a change of the magnetic flux. The change of the flux may be for example an interruption of the magnetic flux between the poles and the rope, when the magnetizing circuits are moved from the closed position to the open position. When the change of the magnetizing circuits from a closed position to an open position is detected, information that indicates the detection may be communicated to the crane controller or to the service centre which are described in FIG. 1. In this way information may be distributed about the opening of the rope monitoring apparatus and the rope may be inspected to determine a cause for the opening and/or to re-install the apparatus by the steps described above. It should be appreciated that a method according to an embodiment may be performed for updating existing equipment with a rope monitoring apparatus described in various embodiments herein. Existing equipment, for example cranes, may have one or more ropes that all may be installed a rope monitoring apparatus described herein. In this way also existing equipment may be provided with the advantages associated with the embodiments described herein.

Figure 8:
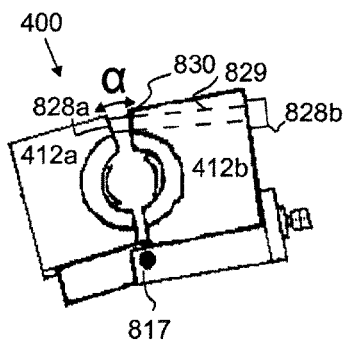
FIG. 8 illustrates a mechanism for moving magnetizing circuits from a closed position to an open position.

FIG. 8 illustrates a mechanism for moving magnetizing circuits from a closed position to an open position. The mechanism may be a hinging mechanism for example. The magnetizing circuits may be installed into an apparatus 400 for monitoring a condition of rope illustrated in FIG. 4b. The mechanism is now explained with reference to the apparatus 400, where the mechanism is installed to operate with the bodies 412a, 412b that comprise the magnetizing circuits. One of the bodies 412b includes a passage 829 that extends between the opposite bodies. Preferably, the passage is located remote from a pivoting point 817 of the bodies, when the bodies are moved between the closed position and the open position. The pivoting point may be the pin as described in FIG. 4b. The remote location may be provided by positioning the passage at the opposite side than the pin with respect to the body. One end of the passage is located between the bodies, when the bodies are in their closed position, and the other end of the passage is at an outer surface of the body, such that it may be reached by maintenance personnel.

A longitudinal part 830 extends through the length of the passage. The longitudinal part may be supported within the passage and to its current position in the passage by threads. Accordingly, the passage and the longitudinal part maybe threaded such that the longitudinal part may be moved into and/or out of the passage by rotating the longitudinal part. One end 828b of the longitudinal part is accessible from the outer surface of the body. In an embodiment, the end of the longitudinal part that is accessible from the outer surface of the body emerges from the passage to the outer surface. In this way the longitudinal part may be operated from the outer surface. In one example, the longitudinal part may be a bolt. The end of the bolt extends to the outer surface such that the bolt may be rotated.

Another end 828a of the longitudinal part emerges from the passage and communicates with the opposite body 412a. The longitudinal part is moved out of the end of the passage between the bodies, whereby the bodies are pivoted to an angle α by the longitudinal part pushing the other body. As the longitudinal part is moved out further, it pushes the other body, and the bodies are pivoted to an angle R, where the bodies are moved from an closed position to an open position similar as explained above with FIGS. 4a, 5, 6 and 6b. The movement of the longitudinal part through the passage may be provided by rotating the longitudinal part, when the passage and longitudinal part are connected by threads. The described mechanism may be used in a method according to an embodiment to open the magnetizing circuits.

The mechanism described above in FIG. 8 may also be used to moving the magnetizing circuits from the open position to the closed position, when the longitudinal part is sufficiently, for example halfway, emerged from the passage towards the opposite body. Referring now to the inclined surfaces 623, 625 of FIG. 6 for describing the operation of the longitudinal part when closing the magnetizing circuits. When the bodies are in the open position the enforcing element communicates with the inclined surface remote from the bodies and/or the rope. When, the bodies are pressed towards the closed position, the enforcing element is moved to the inclined surface closest to the bodies and/or the rope. Then, the sufficiently emerged longitudinal part contacts the opposite body and prevents the magnetizing circuits from fully closing to the angle α, where a rope between the magnetizing circuits may be saturated by magnetic flux. The full closing of the magnetizing circuits may be provided by rotating the longitudinal part. In this way the full closing of the magnetizing circuits may be performed in a controllable way and impacts and/or damages to the rope between the magnetizing circuits may be prevented.

Figure 9A:
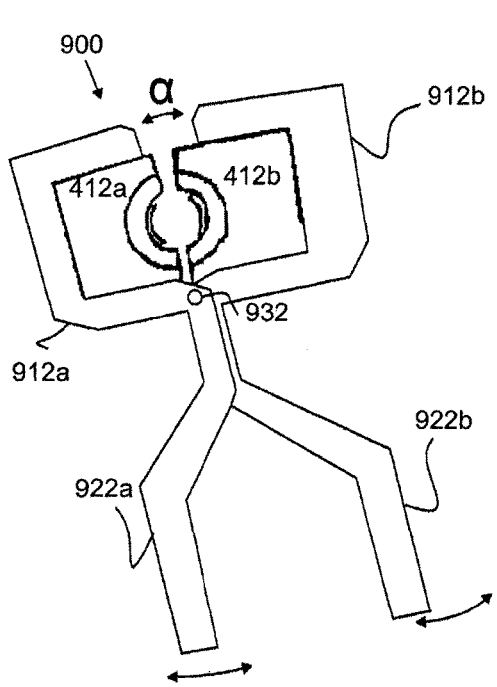
FIGS. 9a and 9b illustrate tools for moving magnetizing circuits between an open position and a closed position, according to embodiments.

FIG. 9a illustrates a tool 900 for moving magnetizing circuits between an open position and a closed position. Accordingly, the tool may be used for both closing and opening the magnetizing circuits. The magnetizing circuits may be installed into an apparatus 400 for monitoring a condition of a rope illustrated in FIG. 4b. The mechanism is now explained with reference to the apparatus 400, where the mechanism is installed to operate with the bodies 412a, 412b that comprise the magnetizing circuits. The tool comprises two gripping parts 912a, 912b that grip the bodies for moving the magnetizing circuits between the different positions. The gripping parts are dimensioned to fit opposite bodies, where the magnetizing circuits are installed. The fitting between the gripping parts and the bodies is preferably close. The close fit is tight enough such that the gripping parts may be sled over each body but the gripping parts are locked to the bodies during pivotal movement of the bodies. The fitting may be provided by suitable dimensioning and shape of the gripping parts and the bodies.

The tool has handles 922a, 922b connected to each gripping part. The handles and gripping parts form pairs that are connected by a hinge 932. Accordingly, the gripping part 912a and the handle 922a form one pair and the gripping part 912b and the handle 922b form another pair. The hinge is preferably positioned on the same axis of pivotal movement as the bodies. Accordingly, the axis may be defined by the pin that hinges the bodies, as in FIG. 4b. The pairs of handles and gripping parts may be overlapping at the hinge, whereby the pin runs through both of the pairs. When the handles are moved towards each other the gripping means are moved away from each other. When the handles are moved apart, the gripping means move towards each other. The movement directions of the handles are illustrated in the FIG. 9a by arrows. Accordingly, the tool may be used for both opening and closing the magnetizing circuits. A controlled method is thus provided for a maintenance operator to open and close magnetizing circuits, and the surface of the rope will not be damaged in the first place during installation of the apparatus around the rope.

Corners of the bodies may provide locking of the bodies to the gripping parts as the gripping parts are pivoted. In an example, a body may have a rectangular shape towards the gripping part and a close fit between the gripping part and the body may be provided. A close fit may comprise a substantially reduced freedom of movement of the fitted parts in at least on one direction. In this way movement of the gripping part and the body may be limited substantially to sliding each gripping part on and/or off the body and limiting the movement in the direction of the pivotal movement of the gripping parts. In one example, the bodies may have rectangular shapes, whereby the rectangular corners may provide the locking. This shaping of corresponding surfaces provides a possibility to transfer enough torque around hinge 932 to open and close the magnetizing circuits.

Accordingly, a tool may comprise gripping parts fitted to bodies that have rectangular shapes towards the gripping parts, whereby a pivoting movement of the gripping parts locks the bodies to the gripping parts. The tool provides moving the bodies between the closed position and the open position without directly touching the bodies. Since no touching is needed, accidents due to electric shocks from the magnetizing circuits and/or injuries to fingers getting between the bodies that are pressed together may be avoided. This is particularly useful, when electromagnets are used in the magnetizing circuits.

The tool provides opening and closing of the magnetizing circuits installed to the body parts particularly in situations, where the ropes are static and thereby not being used to lifting or lowering payload. Accordingly, while apparatuses described in various embodiments provide continuous monitoring of the condition of the ropes, when payload is handled, the tool facilitates maintenance operations of the described apparatuses and the ropes, for example when the apparatus is installed or removed from the ropes.

It should be appreciated that the opening mechanism illustrated in FIG. 8 and the tool of FIG. 9a may be used in various embodiments described herein. For example, they may be used in the method of FIG. 7, for moving the magnetizing circuits moved between an open and a closed position. In one particular embodiment, the tool of FIG. 9a is used to move the magnetizing circuits illustrated in FIG. 4c between the open position and the closed position. In this embodiment, the band around the bodies may be broken by the pivoting movement of the gripping parts, when the magnetizing circuits are opened. On the other hand, when the magnetizing circuits are moved to the closed position, a new band may be installed around the magnetizing circuits to support them in the closed position. The tool thereby provides control to the opening and/or closing of the magnetizing circuits that are supported in the closed position by one or more bands.

Figure 9B:
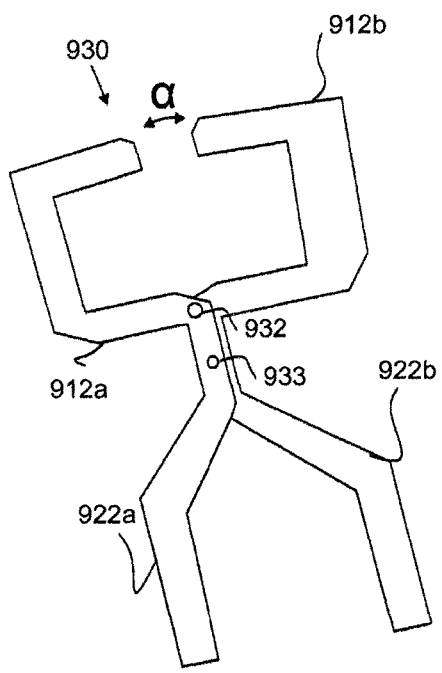

FIG. 9b illustrates a tool 930 for moving magnetizing circuits between an open position and a closed position. The parts of tool corresponds to the parts of the tool of FIG. 9a and the parts further include openings 933 in the handles 922a, 922b. The openings are preferably holes through each of the handles. Preferably, the holes are arranged to the portions of the handles that are overlapping in a closed position of the gripping parts corresponding to the closed position of the magnetizing circuits. When the gripping parts are in the closed position, the openings of the handles are on one another and form a single opening through the handles. Then an object may be inserted to the single opening formed by the handles. The object has a slightly smaller diameter than the single opening and a sufficient length to extend through the single opening. Examples of a suitable object include cylindrical objects or objects having a cylindrical end to be inserted through the single opening, such as a screwdriver or a shaft of a screwdriver. The single opening formed by the openings of the handles provides that the gripping parts may be supported, e.g. locked, to the closed position for example by inserting the screwdriver through the openings, when they are on one another. This is particularly useful in using the tool 930 for installing a band around the magnetizing circuits of FIG. 4c, where the magnetizing circuits are pushed towards the open position by the spring element.

Particularly, when the monitored rope runs in a vertical direction, the handles are substantially horizontal, when the tool is used to move the magnetizing circuits around the rope. Preferably, the dimension of the single hole formed by the holes in the handles is smaller than a handle of the screwdriver such that the screwdriver is supported by the single hole, when the far end, i.e. the end of the screwdriver remote from the person using the screwdriver, is inserted from above to the single hole. Accordingly, the gripping parts may be supported to the closed position, and the person using the tool can perform other tasks, for example installing a band around the magnetizing circuits, as illustrated in FIG. 4c.

Figure 10:
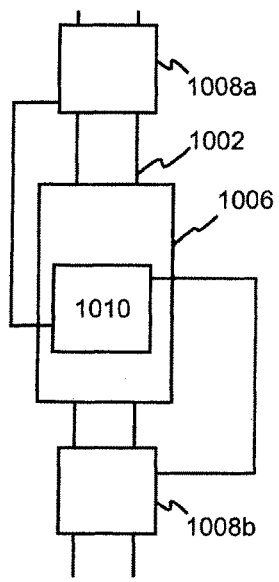
FIG. 10 illustrates an apparatus comprising a fault detector, according to an embodiment.

FIG. 10 illustrates an apparatus 1006 comprising a fault detector 1008a, 1008b, according to an embodiment. The apparatus may be an apparatus described in various embodiments above, for example in FIG. 4. The fault detector is external to the apparatus. Accordingly the apparatus is for monitoring a condition of an elongated ferrous object 1002, for example a rope, having a longitudinal axis. The apparatus comprises two magnetizing circuits comprising magnetic poles arranged along the longitudinal axis, and a magnetic flux guide connecting the poles, said magnetizing circuits being arranged around the object at opposite sides along the longitudinal axis, wherein the magnetizing circuits are hinged together to be movable between a closed position, where the monitored object is enclosed between the poles of the magnetizing circuits and an open position, where monitored object is removable from the apparatus. The apparatus comprises at least one enforcing element operatively connected to the magnetizing circuits such that, in the closed position, the magnetizing circuits are pressed towards each other; and the operative connection between the enforcing element and the magnetizing circuits is caused to disconnect on the basis of detecting a faulty portion of the rope by a force received from a faulty portion of the rope. Preferably the force is perpendicular to the direction of the passage and/or to the travelling direction of the rope. The force may be received, when the rope is moving through the magnetizing circuits.

The faulty portion of the rope may be detected by a fault detector. A fault detector may be internal to the apparatus or external to the apparatus. A surface of the apparatus that receives a force from a faulty portion the rope may serve as a fault detector. Accordingly a passage or openings to the passage between the magnetizing circuits may serve as a fault detector.

The operative connection between the enforcing element and the magnetizing circuits may be disconnected, when the magnetizing circuits are pivoted or moved from the closed position to the open position. The magnetizing circuits may be pivoted or moved from the closed position to the open position by a force received from a faulty portion of the rope entering between the magnetizing circuits or to the fault detector. Accordingly, the force may be received by the fault detector that is internal or external to the apparatus. The force may be received as an electrical force, mechanical force, pneumatic force, hydraulic force. An electrical force may be provided by various sensors without contacting the rope. In one example an electrical force, for example measured in voltages, may be provided, by an optical sensor or a sensor measuring an induced current, for example eddy current.

The fault detector may be located at least on one side of the apparatus, where the rope enters the apparatus. The fault detector may be located on both sides of the apparatus, where the rope enters the apparatus. The sides are vertically spaced by the apparatus extending in the direction of the rope. Accordingly, the apparatus may comprise one or two fault detectors for monitoring the rope in travelling directions of the rope.

The apparatus may comprise a mechanism 1010 for moving magnetizing circuits from a closed position to an open position. The mechanism may be the mechanism described in FIG. 8, for example. Further examples of the mechanisms are described below with reference to FIGS. 11*a*, 11*b*, 12*a* and 12*b*. The fault detector may be connected to the mechanism, for example to the enforcing element in the mechanism, for moving the magnetizing circuits from a closed position to an open position. Accordingly, the fault detecfor may cause the mechanism to move the magnetizing circuits from the closed position to the open position, when a faulty portion is detected.

The fault detector may be implemented as an electrical, mechanical, hydraulic or pneumatic device, or as any combination of mechanical, hydraulic or pneumatic parts. Preferably the fault detector is a non-contacting device that does not physically contact the rope. In this way the fault detector may be adapted more easily to ropes of different diameters. When the fault detector detects a faulty rope, the fault detector may communicate with the mechanism for moving magnetizing circuits from the closed position to the open position. The communications may be performed over a mechanical, electrical, hydraulic or a pneumatic connection, or their combinations.

In one example, the fault detector may comprise a sensor for detecting a faulty rope. The sensor may be an electrical, optical, a mechanical and/or a pressure sensor. The pressure sensor may detect a pressure as a hydraulic pressure or pneumatic pressure for example. An electrical sensor may be based on measuring an induced current, for example eddy current, whereby a faulty rope may be detected by an electrical force resulting from the sensor measuring the rope.

An electrical sensor may be implemented by one or more conductors, for example coils. The conductors may be arranged at least partially around the rope or completely around the rope. A conductor arranged partially around the rope may be located next to the rope at a distance that allows the sensor to detect a faulty rope. The sensor may perform active or passive measurements on the rope. In an active measurement a measurement signal is fed to the conductors and changes to the measurement signal are measured to determine a faulty rope. In a passive measurement, the conductors act as receivers of electrical energy. A faulty portion of the rope may be determined on the basis of one or more changes of the received electrical energy. The electrical energy may be measured by a voltage value, for example.

Figure 11A:
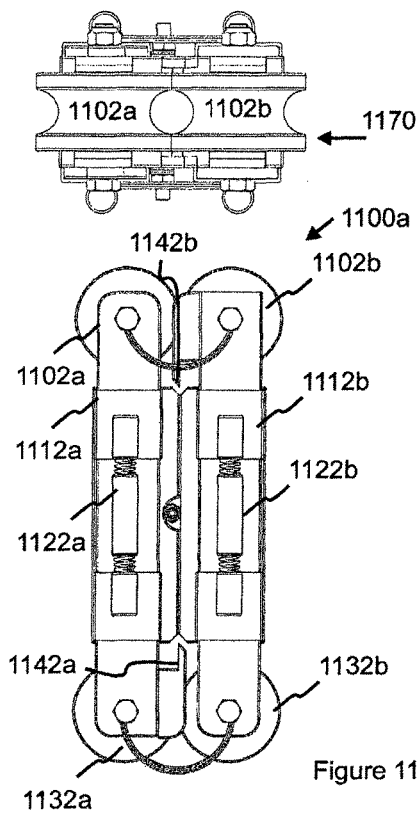
FIGS. 11a, 11b illustrate examples of mechanisms controllable by fault detectors for moving magnetizing circuits from a closed position to an open position, according to embodiments.
Figure 11B:
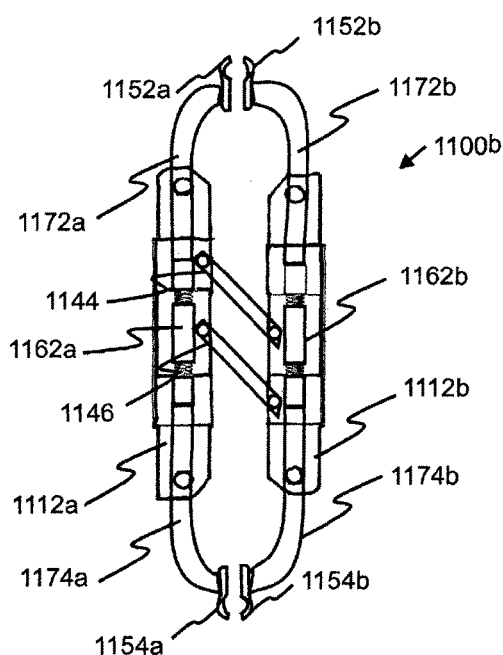
Figure 12A:
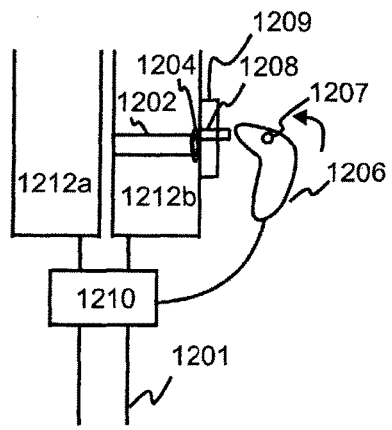
FIGS. 12a and 12b illustrate examples of mechanisms for moving magnetizing circuits from a closed position to an open position, according to embodiments.
Figure 12B:
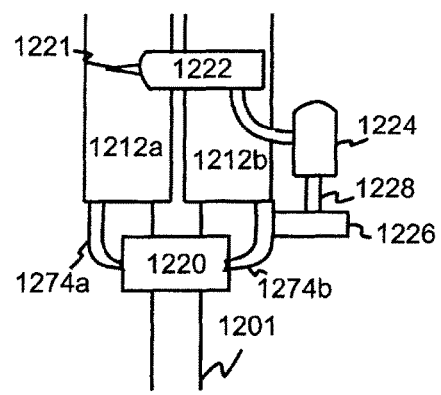

FIGS. 11*a*, 11*b* illustrate examples of mechanisms controllable by fault detectors for moving magnetizing circuits from a closed position to an open position, according to embodiments. FIGS. 12*a* and 12*b* illustrate examples of mechanisms for moving magnetizing circuits from a closed position to an open position, according to embodiments. The mechanisms may be used in the monitoring apparatus of FIG. 10, and be controlled by fault detectors.

Referring to FIGS. 11*a* and 11*b*, an apparatus 1100*a*, 1100*b*, for example the monitoring apparatus described with FIG. 10, includes magnetizing circuits 1112*a*, 1112*b*. In FIG. 11*a*, the magnetizing circuits are in the closed position and in FIG. 11*b* the magnetizing circuits are in the open position. FIGS. 11*a* and 11*b* illustrated different mechanisms for moving the magnetizing circuits from the closed position to the open position. In FIG. 11*a*, the mechanism includes rollers 1102*a*, 1102*b*, 1132*a*, 1132*b* in both ends of both magnetizing circuits. The rollers guide a rope to a passage between the magnetizing circuits. Item 1170 shows a view from one end of the magnetizing circuits. An opening between the rollers guides the rope to the passage. The rollers have U-shaped grooves that form a funnel. Wedges 1142*a*, 1142*b* are positioned in connection with the rollers. The wedges are movable by a faulty portion of the rope between the magnetizing circuits. Accordingly, when a faulty rope enters between the rollers, the rollers and the associated wedge act as a fault detector such that the faulty portion exerts a force to the rollers, whereby the wedge is forced between the magnetizing circuits. The wedge forces the magnetizing circuits from the closed position illustrated in FIG. 11*a* to the open position. In this way, the rollers and wedge on each side of the magnetizing circuits act as fault detectors.

Rollers provide that a faulty rope having an enlarged diameter entering between the rollers causes the rollers to rotate, whereby the faulty rope may be gradually be pressed against the rollers. The faulty rope causes a force to the roller that is substantially perpendicular to the longitudinal direction. Since the rollers are rotated by the faulty rope, they may wear less during use compared to other surfaces that are static and on which the faulty rope slides.

In FIG. 11*b*, the mechanism includes sleeves in each end of the magnetizing circuits. Each of the sleeves is formed by two halves 1152*a*, 1152*b*, 1154*a*, 1154*b* that form a passage for the rope. The sleeves enclose the rope that passes between the sleeves substantially around the diameter of the rope. Each of the sleeve-halves are connected to an enforcing element 1162*a*, 1162*b* by elongated parts 1172*a*, 1172*b*, 1174*a*, 1174*b* that extend longitudinally from the ends of the magnetizing circuits. The sleeve-halves are connected to enforcing elements by the elongated parts for communicating a force from a faulty rope entering the sleeve-halves to the enforcing elements. Accordingly, the sleeves and the elongated parts act as fault detectors such that when a faulty rope enters between the sleeve-halves, the faulty portion exerts a force to the sleeve-halves. The sleeve-halves communicate the force to the enforcing element, whereby the magnetizing circuits are moved from the closed position to the open position illustrated in FIG. 11*b*.

Referring to FIG. 11*b*, the mechanism for moving magnetizing circuits from a closed position to an open position may comprise a four-bar mechanism. The mechanism comprises bars 1144, 1146 that in the open position are sloped with respect to the direction of the rope, i.e. to the longitudinal direction. The bars of the four bar mechanism may include the bars 1144 and 1146 and the magnetizing circuits 1112*a*, 1112*b* (or body halves including the magnetizing circuits) acting as bars. The bars 1144 and 1146 are connected to the magnetizing circuits by joints that provide movement of the bars 1144, 1146 around axes that are perpendicular to the longitudinal direction, i.e. direction for the rope. The sloping of the bars is illustrated in FIG. 11*b*. In the closed position, the bars are aligned or at least more aligned than in the open position with the direction of the rope, i.e. the longitudinal direction. The four-bar mechanism may be operated by the fault detector and/or mechanisms illustrated in FIGS. 11a and 11b. Now referring to the mechanism of FIG. 11a, when the wedge is forced between the magnetizing circuits by a faulty rope, an enforcing element 1122a, 1122b is pressed. The enforcing element communicates with the bars of the four-bar mechanism and causes the bars to move towards a perpendicular angle with respect to the longitudinal direction and in a slope with respect to the direction of the rope. The pressing operation between one or more bars may be arranged by the enforcing element, for example a spring element communicating with a cam operating one or more of the bars. The cam is described for example in FIG. 5. As a skilled person understands that for operating the bars with the cam as described in FIG. 5, the cam may be rotated around a shaft such that the cam is hinged to act around an axis that is perpendicular to the direction of the rope. Preferably the axis or shaft is aligned with the direction of axes of the bars 1144, 1146 that connect to the magnetizing circuits in the four-bar mechanism. Similarly, now referring to the mechanism of FIG. 11b, when a faulty rope enters between the sleeves-halves, the sleeve-halves exert a force on the enforcing element that may communicate with the bars as described above, and cause opening of the magnetizing circuits.

FIGS. 12a and 12b illustrate examples of mechanisms for moving magnetizing circuits 1212a, 1212b from a closed position to an open position, according to embodiments. FIG. 12a illustrates a mechanism that is based on a chemical operation. FIG. 12b illustrates a mechanism that is based on a pneumatic or hydraulic pressure operated actuator.

Now referring to a chemical procedure as illustrated in FIG. 12a, in which the mechanism the mechanism comprises a trigger device 1206 that has a striking pin 1208. The trigger device communicates with a fault detector 1210. The fault detector may have the fault detector described above e.g. in FIG. 10 or in FIG. 11a or 11b. When the fault detector detects a faulty rope 1201, the fault detector communicates a result of the detection to the triggering device. The triggering device and the fault detector may be connected by an electrical, mechanical, pneumatic or hydraulic connection. The result of the fault detector causes the striking pin of the trigger device to hit against a rim 1204 of the rimfire cartridge 1202. The trigger device may hit the rim by rotating around an axis 1207 similar to a hammer hitting a nail. The rim includes a detonating primer, which is ignited by the striking pin that hits the rim after the faulty rope has been detected by the fault detector. The striking pin and the rimfire cartridge may be located within the magnetizing circuits. The magnetizing circuits may comprise a chamber for the rimfire cartridge and a hole for the striking pin. The chamber and the hole may be connected such that the striking pin may hit the rim of the rimfire cartridge. When the striking pin hits the rim, the detonator is ignited, whereby a pressure wave is caused and the magnetizing circuits may be moved from the closed position to the open position. The pressure wave is dimensioned properly to push the magnetizing circuits to the open position.

An extractor (not shown) may be used to extract the rim fire cartridge from the chamber after the detonator has been ignited. There is a supporting piece 1209 that supports the rim of the cartridge 1202, so that during firing recoil does not push the cartridge out of the chamber. The striking pin 1208 is fitted to hit through a hole provided in the supporting piece. Examples of the rimfire cartridges include rifle cartridges that include a rim for detonating the cartridge. A rimfire cartridge can usually be provided with less expense than a centerfire cartridge. An example of useful centerfire cartridge could be based on a revolver of caliber 38 Special, that is loaded for a blank revolver. An example of rimfire cartridge is a HILTI nail gun cartridge, or 22LR (long rifle), that is loaded without a bullet, and may be used as a blank cartridge.

An useful formula in a cartridge comprises a detonating primer, burning powder and a wad to seal the mouth of a shell, in which these components are loaded. If the primer is strong enough, then powder can be excluded.

Now referring to FIG. 12b, the mechanism comprises a pressure actuator 1222 that has a pin 1221 that is operated by a pressure caused by a fault detector 1220 detecting a faulty rope 1201. The fault detector may the fault detector described above e.g. in FIG. 10 or FIG. 11a or 11b. When the fault detector detects a faulty rope, the fault detector communicates a result of the detection to a hydraulic or pneumatic circuit 1224 that causes the pressure actuator to push the pin and cause magnetizing circuits 1212a, 1212b to move from the closed position to the open position. The fault detector may be connected to the hydraulic or pneumatic circuit by one or more bars 1274a, 1274b that are movable in a longitudinal direction of the rope such that a faulty portion of the rope causes a longitudinal movement of the bar. The bars may be the bars as described in in FIG. 11b. A member 1226 that extends perpendicularly outwards from the longitudinal direction and the magnetizing circuits may be connected at least to one 1274b of the bars such that the hydraulic or pneumatic circuit may connect to the member parallel to the magnetizing circuits in the longitudinal direction, whereby the movement of the bars may be communicated to the hydraulic or pneumatic circuit. In the hydraulic or pneumatic circuit the movement of the bars may be converted to pressure in the hydraulic or pneumatic circuit. The pressure is communicated by the circuit to the pressure actuator, whereby the magnetizing circuits may be moved from the closed position to the open position. The hydraulic or pneumatic circuit may be connected to the member by a piston 1228 that is operated by the member.

Figure 13:
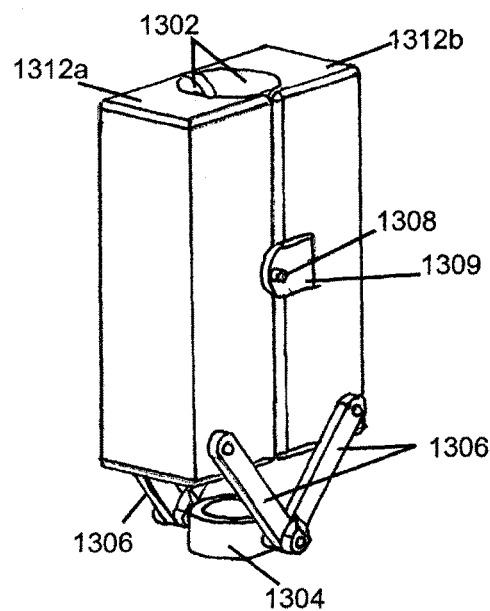
FIG. 13 illustrates an example of a mechanism controllable by a fault detector for moving magnetizing circuits from a closed position to an open position, according to an embodiment.

FIG. 13 illustrates an example of a mechanism controllable by a fault detector for moving magnetizing circuits from a closed position to an open position, according to an embodiment. The magnetizing circuits 1312a, 1312b are illustrated in the closed position. A passage is located between the magnetizing circuits for a rope to travel from one side of the apparatus to another side of the apparatus. Preferably, the passage has cone shaped openings as described with reference to FIGS. 3a, 4b, 4c and 5 such that the diameter of the passage is the largest at the mouth of the passage and is decreased towards the mid-portion. Accordingly, the tip of the opening is inwards to the apparatus. In this way the opening guides the rope to the passage. Although in FIG. 13 only one sleeve is illustrated a further sleeve may be arranged in a similar manner to the opposite side of the apparatus in the longitudinal direction such that there are sleeves arranged on both ends of the passage.

The apparatus has at least one a sleeve 1304 connected by bars 1306 to the magnetizing circuits. The sleeve may be formed from two halves that may be formed from two pieces having a form that may look like the letter 'C'. Accordingly the sleeve may be formed by two opposite pieces of C-letters, where one of the pieces is positioned as a mirror image of the other. The bars position the sleeve in front of the opening from the passage. In the closed position of the magnetizing circuits, the bars may be sloped to a longitudinal direction, i.e. the direction of the rope. A rope entering the apparatus is guided to the passage through the sleeve. When a faulty rope enters the sleeve, the faulty portion causes a force to the sleeve. The sleeve is pressed towards the opening by the faulty rope, whereby the sleeve presses the bars. The bars communicate the force from the sleeve to a movement of the magnetizing circuits from the closed position to the open position. In the open position the bars have been moved towards a perpendicular angle with respect to the longitudinal direction.

A pin 1308 that is adjustable in an axial direction may be disposed to at least one of the magnetizing circuits. The pin may connect the magnetizing circuits in the closed position. The pin may be disposed on a sheet 1309 of metal that extends from one magnetizing circuit to another magnetizing circuit on their outer surface. A tip of the pin may extend to a small hole in the surface of the magnetizing circuit such that the pin generates a resistive force against moving the magnetizing circuits from the closed position to an open position. In an embodiment the pin may be connected to a spring-loaded roller such that the resistive force generated by the pin may be adjusted more easily. The spring-loaded roller may be installed to the tip of the pin. On the other hand the pin may be formed by spring-loaded roller. The roller may act against surface of the hole such that the roller communicates a spring force to the hole. The spring force resists moving the magnetizing circuits from the closed position to the open position. In one example the sheet of metal may provide the spring force, whereby the spring force may be adjusted by selecting dimensions and material of the sheet of metal. The roller provides that movement of the magnetizing circuits from the closed position to the open position takes place smoothly without breaking the magnetizing circuits or the pin. The smooth transition allows adjusting the resistive force accurately to a desired level.

Figure 14:
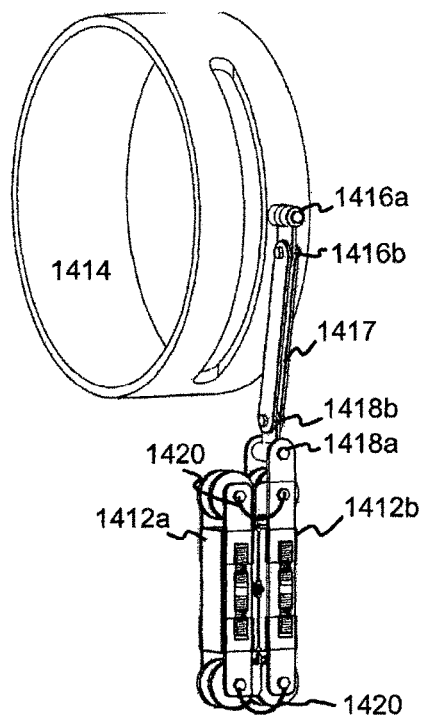
FIG. 14 illustrates an apparatus mounted to a rope guide, according to an embodiment.

FIG. 14 illustrates an apparatus mounted to a rope guide 1414, according to an embodiment. The apparatus may be the apparatus described with FIG. 10 or 11a for example. Magnetizing circuits 1412a, 1412b are illustrated in a closed position. A rope guide may be mounted to the magnetizing circuits via a connecting arrangement 1417 installed to at least one of the magnetizing circuits. The connecting arrangement maybe installed on one end of the magnetizing circuits, where the rope enters to a passage formed by the magnetizing circuits. The connecting arrangement may comprise a bar 1417 that extends between the rope guide and at least one of the magnetizing circuits. The bar may be rotatable around at least two axes 1416a, 1416b 1418a, 1418b at each end of the bar. The axes at each end of the bars are perpendicular to a longitudinal direction, i.e. a direction of the rope. The axes are also perpendicular to each other. The bar provides that on moving the magnetizing circuits from the closed position to the open position, the magnetizing circuit connected to the bar does not fall to the ground and cause danger to people. In the open position the magnetizing circuits may stay connected to each other by a cable 1420. In this way it may be sufficient to connect only one of the magnetizing circuits to the rope guide in order to prevent the magnetizing circuits from falling down to the ground. The magnetizing circuits may be connected to each other, by a hinging mechanism or bars as described in various embodiments above in order to prevent falling of the magnetizing circuits to the ground in the open position.

An apparatus for monitoring according to an embodiment may be installed to a crane including one or more ropes for hoisting payload. The crane may be further equipped with a rope monitoring arrangement according to an embodiment. The crane may be a gantry crane or a bridge crane for example. A single rope may be installed with more than one, i.e. a plurality of monitoring apparatuses described above.

The apparatus according to an embodiment may also be installed to various other arrangements including a hoisting machinery, in addition to the cranes, where ropes are used to hoist payload. These arrangements include but are not limited to a ropeway, an elevator, a conveyor in a mine shaft and a ski lift.

It should be appreciated that in various embodiments the monitoring apparatus moves with respect to the rope. This means that depending on implementation, the rope may move through the apparatus, while the apparatus is stationary. On the other hand the rope may be stationary while the apparatus moves. Further, on the other hand, both the apparatus and the rope may move and they move with respect to each other such that the rope travels through the apparatus.

An embodiment provides a method for removing a monitored object from an apparatus for monitoring a condition of an elongated ferrous object having a longitudinal axis. The monitoring apparatus includes two magnetizing circuits including magnetic poles arranged along the longitudinal axis, and a magnetic flux guide connecting the poles, said magnetizing circuits being arranged around the object at opposite sides along the longitudinal axis, wherein the magnetizing circuits are hinged together to be movable between a closed position, where the monitored object is enclosed between the poles of the magnetizing circuits and an open position, where monitored object is removable from the apparatus, the apparatus comprises a spring element operatively connected to the magnetizing circuits. The method comprises pressing the magnetizing circuits towards each other, by the operative connection in the closed position of the magnetizing circuits, and disconnecting the operative connection between the spring element and the magnetizing circuits, by pivoting the magnetizing circuits from the closed position to the open position. The disconnection of the magnetizing circuits may be achieved by movement of the magnetizing circuits by a faulty rope and/or a foreign object attached to the rope as described in various embodiments above.

Various embodiments comprise two operative connections between an enforcing element operatively connected to the magnetizing circuits. A first operative connection provides that in the closed position of the magnetizing circuits, the magnetizing circuits are pressed towards each other. When the magnetizing circuits are pivoted from the closed position to the open position, the first operative connection between the enforcing element and the magnetizing circuits is disconnected. The enforcing element and the magnetizing circuits may have a second operative connection, when the magnetizing circuits are in the open position. In the second operative connection the enforcing element, the magnetizing circuits are pivoted apart from each other by the force exerted from the enforcing element. Accordingly, the operative connections in the open position of the magnetizing circuits and in the closed position of the magnetizing circuits are different and the operative connection of a previous position is disconnected, when the magnetizing circuits are moved from one position to another, where a current operative connection is formed according to the current position of the magnetizing circuits, i.e. the open position or the closed position. The two operative connections may be provided by a cam having a plurality of surfaces that communicate with the enforcing element to receive the force exerted by the enforcing element. Preferably, the plurality of surfaces comprise at least one surface that communicates with the enforcing element in the open position of the magnetizing circuits and at least one surface that communicates with the enforcing element in the closed position of the magnetizing circuits.

The steps/points, and related functions described above in FIG. 7 are in no absolute chronological order, and some of the steps/points may be performed simultaneously or in an order differing from the given one. Other functions can also be executed between the steps/points or within the steps/points and other signalling messages sent between the illustrated messages. Some of the steps/points or part of the steps/points can also be left out or replaced by a corresponding step/point or part of the step/point.

It will be obvious to a person skilled in the art that, as the technology advances, the inventive concept can be implemented in various ways. The invention and its embodiments are not limited to the examples described above but may vary within the scope of the claims.

The invention claimed is:

1. An apparatus for monitoring a condition of an elongated ferrous object having a longitudinal axis, said apparatus comprising:
   two magnetizing circuits comprising magnetic poles arranged along the longitudinal axis, and a magnetic flux guide connecting the poles, said magnetizing circuits being arranged around the object at opposite sides along the longitudinal axis, wherein the magnetizing circuits are hinged together to be movable between a closed position, where the monitored object is enclosed between the poles of the magnetizing circuits and an open position, where the monitored object is removable from the apparatus; and
   an enforcing element operatively connected to the magnetizing circuits such that, in the closed position, the magnetizing circuits are pressed towards each other, and the operative connection between the enforcing element and the magnetizing circuits is caused to disconnect on the basis of detecting a faulty portion of the longitudinal ferrous object by a force received from the faulty portion of the longitudinal ferrous object.

2. The apparatus according to claim 1, wherein the operative connection between the enforcing element and the magnetizing circuits is disconnected, when the magnetizing circuits are pivoted from the closed position to the open position.

3. The apparatus according to claim 1, wherein the magnetizing circuits are pivoted from the closed position to the open position by a force received from a faulty portion of the longitudinal ferrous object entering between the magnetizing circuits.

4. The apparatus according to claim 1, wherein the faulty portion is detected by a fault detector that is operatively connected to the enforcing element for moving the magnetizing circuits from the closed position to the open position.

5. The apparatus according to claim 4, wherein the fault detector comprises an electrical, optical, mechanical, pneumatic or hydraulic sensor.

6. The apparatus according to claim 4, wherein the apparatus comprises a mechanism for moving magnetizing circuits from the closed position to the open position, wherein the mechanism is controllable by the fault detector.

7. The apparatus according to claim 6, wherein the mechanism comprises a wedge movable by a faulty portion of the elongated ferrous object between the magnetizing circuits, sleeve-halves connected to enforcing elements in the magnetizing circuits for communicating a force from a faulty elongated ferrous object entering the sleeve-halves to the enforcing elements, and a trigger device having a striking pin for igniting a detonating primer or a pressure actuator.

8. The apparatus according to claim 1, where the operative connection between the enforcing element and the magnetizing circuits is disconnected in the open position, when the magnetizing circuits are at an angle that is smaller than an angle allowing removal of the object.

9. The apparatus according to claim 1, wherein the open position of the magnetizing circuits includes angles, where the magnetizing circuits are separable at least by a diameter of the monitored object to allow removal of the object.

10. The apparatus according to claim 1, further comprising:
    a cam extending between the enforcing element and one of the magnetizing circuits,
    wherein a first end of the cam is connected to the first magnetizing circuit and a second end of the cam has a surface that communicates with the enforcing element to receive the force exerted by the enforcing element, said surface being movable with respect to the enforcing element to receive the force exerted by the enforcing element in different locations along the surface, wherein when the first and the second magnetizing circuits are in the closed position, said surface extends in a direction of an increasing force from the enforcing element being communicated to the surface by the movement of the surface with respect to the enforcing element and up to a length of the surface, where the magnetizing circuits are moved to the open position and the force communicated from the enforcing element to the first surface is decreased.

11. The apparatus according to claim 10, wherein the second end of the cam has a plurality of surfaces that communicate with the enforcing element to receive the force exerted by the enforcing element, and said surfaces being movable with respect to the enforcing element to receive the force exerted by the enforcing element in different locations along the surfaces, wherein when the first and the second magnetizing circuits are in the closed position a first surface communicates with the enforcing element, and when the first and the second magnetizing circuits are in the open position, a second surface communicates with the enforcing element.

12. The apparatus according to claim 11, wherein the first and the second surface define corresponding operative connections between the enforcing element and the magnetizing circuits.

13. The apparatus according to claim 11, wherein the second surface extends in a direction of decreasing force being received from the enforcing element by the movement of the second surface with respect to the enforcing element, when the magnetizing circuits are moved apart in the open position.

14. The apparatus according to claim 10, wherein the second end of the cam and the enforcing element are fixed to different magnetizing circuits and arranged movable with respect to each other by a rotatable part that is connected to the enforcing element to act between the enforcing element and the cam, whereby the movement of the magnetizing circuits is communicated between the cam and the enforcing element by the movement of the rotatable part on the surface of the cam.

15. The apparatus according to claim 1, wherein the elongated ferrous object comprises a rope of a hoisting machinery, including a hoisting machinery in a crane, a ropeway, an elevator, a conveyor in a mine shaft and a ski lift.

16. The apparatus according to claim 1, wherein the magnetizing circuits are arranged to move from the closed position towards the open position by a force received from a faulty portion of the longitudinal ferrous object entering between the magnetizing circuits, said force exceeding the force communicated from the enforcing element to the magnetizing circuits and/or a magnetic force exerted by the magnetizing circuits to the longitudinal ferrous object.

17. The apparatus according to claim 1, wherein the magnetizing circuits form a passage for the elongated ferrous object, wherein the passage comprises a mid-portion between two ends whose diameter is decreased towards the mid-section.

18. The apparatus according to claim 1, wherein the enforcing element comprises a pneumatic circuit, a hydraulic circuit and/or a storage of potential energy comprising: a hydraulic accumulator, a pneumatic accumulator, a weight movable along a passage and/or a spring element formed by one or more springs, including disc springs or coil springs, arranged in series.

19. The apparatus according to claim 1, wherein the apparatus comprises an adjustment nut arranged to communicate with the enforcing element such that the force communicated from the enforcing element to the magnetizing circuits may be adjusted.

20. The apparatus according to claim 1, wherein the apparatus comprises rollers arranged such that the magnetizing circuits are positioned between the rollers in the longitudinal direction for guiding the monitored object between the magnetizing circuits.

21. The apparatus according to claim 1, wherein the magnetizing circuits are installed to opposite body halves, wherein a first body halve includes a passage that extends between the opposite body halves, said passage including a first end between the body halves, when the body halves are in their closed position, and said passage including a second end at the outer surface of the first body halve, and a longitudinal part is supported within the passage and to the second body halve, wherein the longitudinal part is movable through the passage to disconnect the magnetizing circuits by the longitudinal part moving the body halves.

22. The apparatus according to claim 1, wherein the enforcing element comprises a band around the magnetizing circuits for supporting the magnetizing circuits to the closed position and a breaking point arranged to the band, wherein the band is broken at the breaking point, when the magnetizing circuits are pivoted from the closed position to the open position, whereby the magnetizing circuits are maintained at the open position.

23. A monitoring arrangement of elongated ferrous objects, comprising an apparatus for monitoring a condition of an elongated ferrous object having a longitudinal axis, said apparatus comprising:

two magnetizing circuits comprising magnetic poles arranged along the longitudinal axis, and a magnetic flux guide connecting the poles, said magnetizing circuits being arranged around the object at opposite sides along the longitudinal axis, wherein the magnetizing circuits are hinged together to be movable between a closed position, where the monitored object is enclosed between the poles of the magnetizing circuits and an open position, where monitored object is removable from the apparatus; and an enforcing element operatively connected to the magnetizing circuits such that, in the closed position, the magnetizing circuits are pressed towards each other, and the operative connection between the enforcing element and the magnetizing circuits is caused to disconnect on the basis of detecting a faulty portion of the longitudinal ferrous object by a force received from the faulty portion of the longitudinal ferrous object, and the monitoring arrangement comprises:

a sensor for measuring magnetic flux, said sensor being connected to the magnetizing circuits; and a controller connected to the sensor and configured to determine a movement of the magnetizing circuits from a closed position to an open position by a change of the magnetic flux.

24. A method by an apparatus or a monitoring arrangement comprising the apparatus, wherein the apparatus is for monitoring a condition of an elongated ferrous object having a longitudinal axis, said apparatus comprising:

two magnetizing circuits comprising magnetic poles arranged along the longitudinal axis, and a magnetic flux guide connecting the poles, said magnetizing circuits being arranged around the object at opposite sides along the longitudinal axis, wherein the magnetizing circuits are hinged together to be movable between a closed position, where the monitored object is enclosed between the poles of the magnetizing circuits and an open position, where monitored object is removable from the apparatus; and an enforcing element operatively connected to the magnetizing circuits such that, in the closed position, the magnetizing circuits are pressed towards each other; and the operative connection between the enforcing element and the magnetizing circuits is caused to disconnect on the basis of detecting a faulty portion of the longitudinal ferrous object by a force received from the faulty portion of the longitudinal ferrous object, wherein the method comprises disconnecting the operative connection between the enforcing element and the magnetizing circuits by pivoting the magnetizing circuits from the closed position to the open position.

25. A payload handling system, comprising:

an elongated ferrous object for hoisting payload; and a monitoring arrangement comprising an apparatus for monitoring a condition of an elongated ferrous object having a longitudinal axis, said apparatus comprising:

two magnetizing circuits comprising magnetic poles arranged along the longitudinal axis, and a magnetic flux guide connecting the poles, said magnetizing circuits being arranged around the object at opposite sides along the longitudinal axis, wherein the magnetizing circuits are hinged together to be movable between a closed position, where the monitored object is enclosed between the poles of the magnetizing circuits and an open position, where monitored object is removable from the apparatus; and an enforcing element operatively connected to the magnetizing circuits such that, in the closed position, the magnetizing circuits are pressed towards each other; and the operative connection between the enforcing element and the magnetizing circuits is caused to disconnect on the basis of detecting a faulty portion of the longitudinal ferrous object by a force received from the faulty portion of the longitudinal ferrous object, wherein the apparatus is attached to the elongated ferrous object when payload is handled by the elongated ferrous object.

\* \* \* \* \*